(12) United States Patent
Cabiri et al.

(10) Patent No.: US 11,116,893 B2
(45) Date of Patent: Sep. 14, 2021

(54) SIMPLIFIED AND/OR ONE-HANDED USE OF A PATCH INJECTOR

(71) Applicant: West Pharma. Services IL, Ltd., Ra'anana (IL)

(72) Inventors: Oz Cabiri, Hod Hasharon (IL); Ran Hezkiahu, Herzliya (IL)

(73) Assignee: WEST PHARMA. SERVICES IL, LTD., Ra'anana (IL)

( * ) Notice: Subject to any disclaimer, the term of this patent is extended or adjusted under 35 U.S.C. 154(b) by 0 days.

(21) Appl. No.: 16/485,693

(22) PCT Filed: Jun. 21, 2017

(86) PCT No.: PCT/US2017/038527
§ 371 (c)(1),
(2) Date: Aug. 13, 2019

(87) PCT Pub. No.: WO2018/151750
PCT Pub. Date: Aug. 23, 2018

(65) Prior Publication Data
US 2019/0381239 A1 Dec. 19, 2019

Related U.S. Application Data

(60) Provisional application No. 62/458,841, filed on Feb. 14, 2017.

(51) Int. Cl.
*A61M 5/142* (2006.01)
*A61M 5/158* (2006.01)
*A61M 5/00* (2006.01)
*A61M 5/14* (2006.01)

(52) U.S. Cl.
CPC ........ *A61M 5/14248* (2013.01); *A61M 5/158* (2013.01); *A61M 5/002* (2013.01);
(Continued)

(58) Field of Classification Search
CPC .. A61M 5/14248; A61M 5/158; A61M 5/002; A61M 2005/1402; A61M 2005/14256; A61M 2005/1585; A61M 2005/1586; A61M 2005/1403
See application file for complete search history.

(56) References Cited

U.S. PATENT DOCUMENTS 8,727,117 B2 5/2014 Maasarani
9,084,668 B2 7/2015 Hamas
(Continued)

FOREIGN PATENT DOCUMENTS

EP 2878320 A1 6/2015
JP 2013516280 A 5/2013
(Continued)

OTHER PUBLICATIONS

Int'l Preliminary Report on Patentability dated Jul. 10, 2019 in Int'l Application No. PCT/US2017/038527.
(Continued)

*Primary Examiner* — Theodore J Stigell
(74) *Attorney, Agent, or Firm* — Panitch Schwarze Belisario & Nadel LLP

(57) ABSTRACT

A wearable medical device may be unpacked, prepared, and/or used while being grasped with a single hand position. For example, the device may be removed from a package, primed, and/or adhered to the skin of a user while being grasped with the single hand position. Optionally, the device may be used with a single hand. Optionally, the device includes a delivery interface (for example, including a needle tip and/or a skin contact surface). Optionally, the device includes a protector that preserves sterility of the delivery interface. Optionally, the cover can be removed with a single hand. Optionally, removal of the cover is performed with the same hand position as placement of the device on a delivery site.

17 Claims, 10 Drawing Sheets

(52) U.S. Cl.
    CPC .............. *A61M 2005/1402* (2013.01); *A61M 2005/14256* (2013.01); *A61M 2005/1585* (2013.01); *A61M 2005/1586* (2013.01); *A61M 2205/502* (2013.01); *A61M 2205/583* (2013.01); *A61M 2205/586* (2013.01); *A61M 2205/8206* (2013.01)

(56) References Cited

U.S. PATENT DOCUMENTS

2011/0172645 A1    7/2011    Moga et al.
2016/0135895 A1    5/2016    Faasse et al.

FOREIGN PATENT DOCUMENTS

| WO | 2007141210 A1 | | 12/2007 |
|---|---|---|---|
| WO | WO-2007/141210 | * | 12/2007 |
| WO | 2009039013 A1 | | 3/2009 |
| WO | 201154160 A1 | | 5/2011 |
| WO | 2011084951 A2 | | 7/2011 |

OTHER PUBLICATIONS

Office Action dated Mar. 23, 2021 in JP Application No. 2019-543787.
Office Action dated Apr. 14, 2021 in EP Application No. 17734924.8.

* cited by examiner

SIMPLIFIED AND/OR ONE-HANDED USE OF A PATCH INJECTOR

CROSS-REFERENCE TO RELATED APPLICATIONS

This application is a section 371 of International Application No. PCT/US17/38527, filed Jun. 21, 2017, which was published on Aug. 23, 2018 under International Publication No. WO 2018/151750 A1, and which claims the benefit of priority under 35 USC § 119(e) of U.S. Provisional Patent Application No. 62/458,841, filed Feb. 14, 2017, the contents of each of which are incorporated herein by reference in their entirety.

FIELD AND BACKGROUND OF THE INVENTION

The present invention, in some embodiments thereof, relates to a medical device and a method for simplified use of the device and more particularly but not exclusively to a wearable drug delivery device and/or a method of use of the device.

US Patent Application Publication No. 2016/0135895 appears to disclose, "packaging, when assembled, may include any feature or configuration that improves ease of opening the sealed package."

US Patent Application Publication No. 2011/0172645 appears to disclose a "delivery device 16 to deliver a drug to a subject," in which a "protective barrier 14 is removed exposing adhesive layer 22. In the embodiment shown, protective barrier 14 includes a tab 30 that facilitates griping of protective barrier 14 during removal. Once adhesive layer 22 is exposed, delivery device 16 is placed on the skin. Adhesive layer 22 is made from an adhesive material that forms a nonpermanent bond with the skin of sufficient strength to hold delivery device 16 in place on the skin of the subject during use. Cover 12 is released from delivery device 16 exposing housing 18 and button 20 by squeezing the sides of cover 12. With delivery device 16 adhered to the skin of the subject, button 20 is pressed to trigger delivery of the drug to the patient. When delivery of the drug is complete, delivery device 16 may be detached from the skin of the subject by applying sufficient force to overcome the grip generated by adhesive layer 22."

U.S. Pat. No. 9,084,668 appears to disclose "packaging for the delivery of sterile implants, for example, mammary prostheses, in a manner to facilitate handling in the operating room." In some embodiments, an "outer bowl-shaped tray can be easily and securely held in one hand and inverted by gripping with the thumb and at least one finger on opposing gripping surfaces without altering the configuration of the tray."

U.S. Pat. No. 8,727,117 appears to disclose "A package housing a syringe. Packages according to a first aspect of the present invention include a syringe and a blister package surrounding the syringe. The syringe typically will be sterile inside the package. The blister package comprises a flexible web sealed to a backing defining a compartment surrounding the syringe that enables the syringe to be squeezed out of the package. The features providing for removal of the syringe allow the syringe to be removed from the package with only one hand without comprising sterility." Specifically, "referring to FIGS. 5 and 6, the blister package 30 comprises a flexible web 32 sealed to a backing 34 defining a compartment 36 for surrounding the syringe 12 and providing a sealed region 38 about a periphery of the backing 34. The sealed region 38 defines a proximal region seal 40 having a width W1, a distal region seal 42. having a width W2, and a flange region seal 44 having a width W3. The flange region seal width W3 is substantially reduced adjacent the flange region 18 compared to the distal region seal width W2 to enable the syringe to be squeezed out of the package with one hand."

SUMMARY OF THE INVENTION

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

According to an aspect of some embodiments of the invention, there is provided a method of operating a drug delivery device including a gripping interface, a needle with a sterile tip, a cover protecting sterility of the tip and an adhesive skin contact surface including: grasping the gripping interface of the device; removing the cover while continuing the grasping; and adhering the device to the skin of a subject while continuing the grasping.

According to some embodiments of the invention, the removing includes anchoring the cover to an anchor that does not include a human hand and pulling the delivery device away from the anchor.

According to some embodiments of the invention, the needle tip is concealed behind the skin contact surface and wherein the needle tip remains concealed after the removing.

According to some embodiments of the invention, the cover includes an adhesive liner covering the adhesive skin contact surface and wherein the removing peels the adhesive liner from the adhesive skin contact surface.

According to some embodiments of the invention, the delivery device includes a control interface and the grasping is performed with one hand while maintaining at least one digit of the one hand free and positioned to manipulate the control interface.

According to some embodiments of the invention, the control interface includes a button.

According to some embodiments of the invention, the method further includes pushing the button toward the adhesive skin surface.

According to an aspect of some embodiments of the invention, there is provided a method of priming of a drug delivery device for user using one hand, the device including a gripping interface, a sterile delivery interface including an adhesive skin contact surface and a cover retaining a sterility of at least part of the delivery interface, the method including: grasping a gripping interface of the drug delivery device with the one hand while the cover protects sterility of the delivery interface; anchoring the cover to an anchor that does not include a human hand; pulling the drug delivery device away from the anchor to separate the cover from the delivery device the pulling with the one hand while continuing the grasping.

According to some embodiments of the invention, the anchoring includes holding the cover with a mouth.

According to some embodiments of the invention, the at least part of the delivery interface includes a needle tip concealed behind the skin contact surface and wherein the needle tip remains concealed after the cover is separated from the delivery device.

According to some embodiments of the invention, the cover includes an adhesive liner covering the adhesive skin contact surface and wherein the pulling peels the adhesive liner from the adhesive skin contact surface.

According to some embodiments of the invention, the method further includes: adhering a skin contact surface to the skin of the subject while continuing the grasping.

According to some embodiments of the invention, the grasping is performed while the drug delivery device is at least partially inside of a packaging, the method further including: removing the drug delivery device from a package prior to the anchoring while continuing the grasping.

According to some embodiments of the invention, the method further includes opening the package with the one hand prior to the grasping and exposing the gripping interface of the device as a result of the opening.

According to some embodiments of the invention, the delivery device includes a control interface and the grasping is performed while maintaining at least one digit of the one hand free and positioned to manipulate the control interface.

According to an aspect of some embodiments of the invention, there is provided a kit for one-handed delivery of a drug to a subject including: a wearable drug delivery device including an adhesive contact surface configured to adhere the device to the skin of the subject and a grip including opposing gripping surfaces, each opposing gripping surfaces at an angle of between 30 and 150 degrees to the contact surface; a user interface located between the gripping surface; a package holding the device with the adhesive contact surface shielded by the package while the grip and the user interface are exposed.

According to some embodiments of the invention, the kit further includes: a closure to the package, the closure shielding the gripping surfaces and wherein removal of the closure exposes the gripping surfaces while the drug delivery device is at least partially inside of a packaging.

According to some embodiments of the invention, the closure is configured for one handed removal from the package that shields the adhesive contact surface.

According to some embodiments of the invention, the packaging includes a base configured to sit stably on a flat horizontal surface while the user interface is angled between 10 to 50 degrees of the base.

According to some embodiments of the invention, the packaging includes space for inserting a finger between the package and each of the gripping surfaces.

According to some embodiments of the invention, the kit further includes: an orientation indicator visible from outside the package for orienting the delivery device for grasping the grip while the device is still inside the package.

According to some embodiments of the invention, the delivery device includes a delivery interface, the kit further including: a sterility protecting cover, separating between the delivery interface and the grip.

According to some embodiments of the invention, the delivery interface includes a sterile needle tip and the protective cover includes a needle cover.

According to some embodiments of the invention, the needle tip is concealed behind the adhesive contact surface.

According to an aspect of some embodiments of the invention, there is provided a kit for integrated use of a drug delivery device including: a wearable drug delivery device including a grip for holding a device with a palm of a hand facing the device; an adhesive contact surface on a side of the device opposite the grip, the adhesive contact surface configured to adhere the device to a skin of the subject, and a package holding the device with the adhesive contact surface shielded by the package while the grip is exposed, the package including a guide encouraging a user to hold the grip with a preferred finger.

According to some embodiments of the invention, the grip is sized and shaped to be held by a subset of digits of a hand, the wearable drug delivery device further including a user interface sized and shaped to be controlled by a free digit of the hand while the subset of digits hold the grip.

According to some embodiments of the invention, the wearable drug delivery device further includes a user interface sized and shaped to be controlled by a free digit of the hand while the subset of digits hold the grip.

According to some embodiments of the invention, the wearable drug delivery device further includes a priming interface protruding from the skin contact surface.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

DESCRIPTION OF SPECIFIC EMBODIMENTS OF THE INVENTION

Figure 1A:
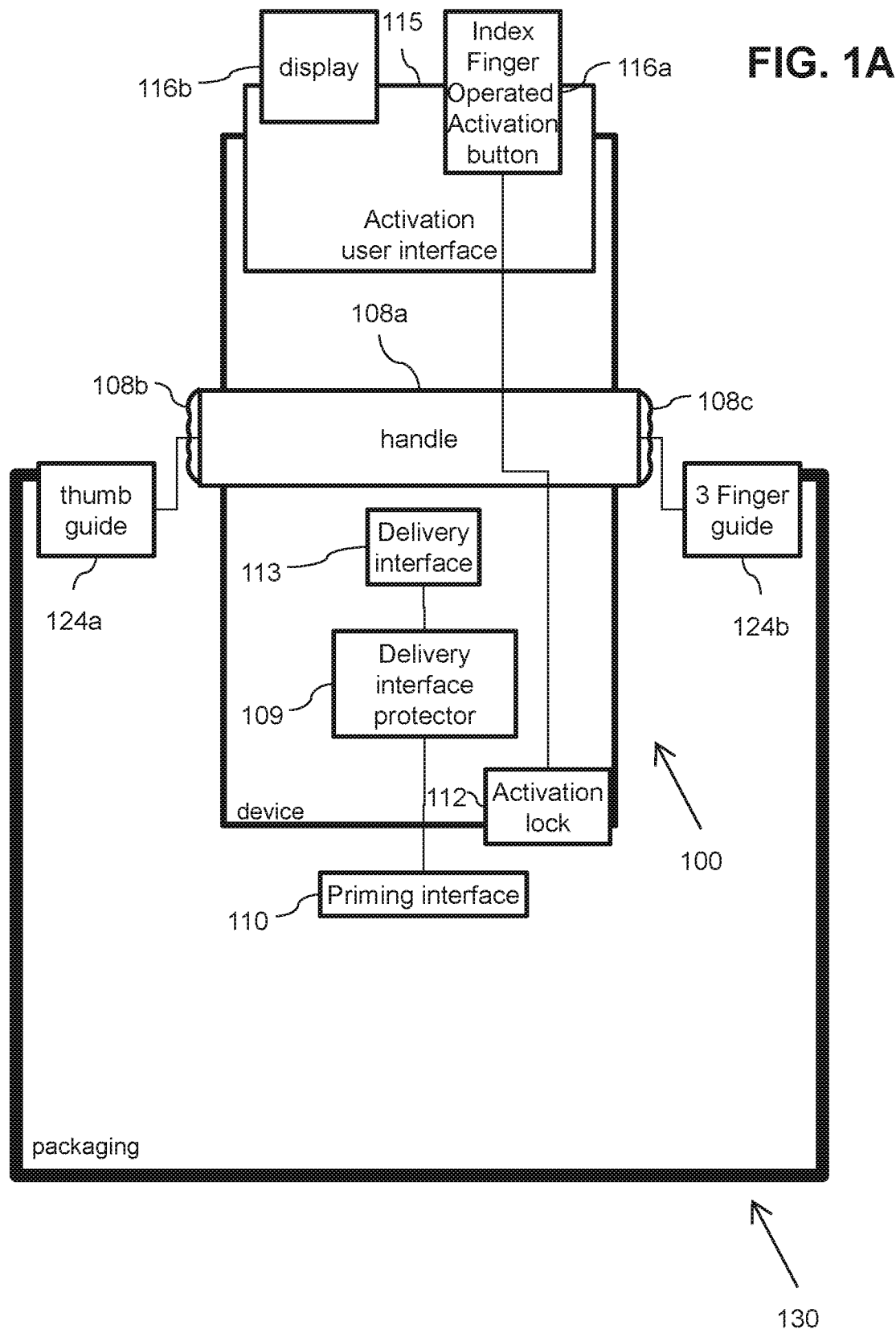
FIG. 1A is a schematic illustration of a device and package in accordance with an embodiment of the current invention.

The present invention, in some embodiments thereof, relates to a medical device and a method for simplified use of the device and more particularly but not exclusively to a wearable drug delivery device and/or a method of use of the device by grasping the device directly from the packaging and/or initiating drug delivery with a single gripping position and/or using only one hand.

Overview

In some embodiments, a wearable drug delivery device allows a user to receive a drug away from the presence of supervisory medical personnel. In some cases, use of a wearable delivery device may allow earlier discharge of a patient from a medical facility. In some cases, early discharge improves quality of life of a patient who may return to family and/or home and/or preferred activities. In some cases, early discharges save money, for example, reducing hospital stays.

An aspect of some embodiments of the present invention relates to integrated use of a wearable drug delivery device by a single hand position deployment. Applicant has performed user studies with prototype drug delivery devices revealing that some users are confused while handling the device. The applicant realized that one possible cause of these problems was improper repositioning of the device at various stages of deployment.

In some applications, the drug delivery device may be designed such that some and/or all user steps in deployment of the device, for example, from the removal of the device from the packaging until delivery of the drug, may be performed while holding the device without changing a hand position on the device. Alternatively or additionally, the user may grasp the device while the sterility of the delivery interface is protected (e.g. before priming the device) and continue holding the device without changing a hand position on the device (for example, until the device is placed onto a delivery site). Optionally, deployment of the device may include various steps and/or user checks, for example to prevent improper and/or accidental deployment. Optionally, all of the steps and/or checks are performed either before removing the device from its packaging and/or while holding the device with a single hand position.

In some embodiments, a user action may be performed before removing the device from its packaging. For example, a device may be powered up in response to opening the device packaging, even before the device is removed from the package. For example, a communication channel of the delivery device may be initiated before the device is removed from its packaging (for example the device may be paired to a wireless network and/or a computing/communication device).

In some embodiments, a user action may be performed while holding the device, without requiring changing hand position on the device. For example, some functions may be performed automatically when the device is removed from a package. For example, a battery isolator and/or a needle cover and/or an adhesive liner may be connected to a packaging of the device such that removing the device from the packaging may power up the device and/or remove the needle cover and/or remove the adhesive liner. Alternatively or additionally, the device may include a magnetic and/or proximity switch. The switch optionally powers up and/or initiates the device when it is removed from the package.

In some embodiments, a user may perform actions while holding the device without changing a hand position. For example, the grip of the device may be designed such that the user grasps the device with some digits of his hand while leaving another digit free to operate a user interface. For example, a user interface of a device may be operated by the free digit without changing his hand position on the device.

In some embodiments, a drug delivery device may include an inertial sensor and/or the user may control the device by moving his hand while holding the device and/or without changing a hand position on the device. In some embodiments, a drug delivery device may include a hands free user interface that is operated with one hand and/or without use of a hand. For example, the device may include a handle that can be pulled by the teeth and/or hooked onto an object and pulled and/or pushed. For example, the device may include a proximity sensor that senses when the device is brought close to a surface, for example an injection zone on the skin of a user. For example, a surface and/or the skin of the injection zone may serve as a counter force for pushing an activation button.

An aspect of some embodiments of the present invention relates to a wearable drug delivery device configured for unpacking, preparing, and/or activating using one hand. In some cases, development of a new drug may be delayed by difficulties finding subjects for user studies. The Applicant recognized that in some cases there are subjects who are ready to join a user study of the drug, but are prevented due to user requirements of a delivery device. For example, a wearable delivery device may limit users to those who can deploy the device for example by requiring two hands in order to unpack, prepare and/or activate the device. In some embodiments, the current invention may allow use of the device by a person with limited or no use of one hard, with only one hand, and/or make it easier to find subjects for user studies.

In some embodiments, the packaging of a device is designed for one-handed use. Optionally, the package is designed to be opened using one hand. For example, the package may sit stably without support on a flat surface. For example, a one handed opening interface may be exposed while the package sits on a flat surface. Optionally, the package is designed such that once the package is open the device is ready to be grasped and/or removed from the package. For example, with the same hand position with which the device was removed from the package the device may be placed on an injection site by a user without changing his hand position. For example, the package may present a dorsal side of the device towards the user and/or have space for the user positioning his fingers around the device while the device rests in the package. Optionally, the device includes a user interface designed to be accessible, visible, and/or worked (for example, by a free digit of a grasping hand) while the user is grasping the device.

In some embodiments, a wearable medical device may include a drug delivery device. Optionally the device may be preloaded. Alternatively or additionally, a drug delivery device may facilitate one-handed loading of a drug cartridge. In some embodiments, preloading the device increases the simplicity of use of the device. Optionally, preloading in addition to integrated one hand position operation may result in a particularly simple user interface. Alternatively or additionally, wearable device may include an injector, (for example, a patch injector), an infuser, a transdermal delivery device, and/or a monitoring device. In some embodiments, a wearable medical device is single use and/or self-administered.

Detailed Embodiments

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Integrated and/or One Handed use of a Drug Delivery Device

Figure 1B:
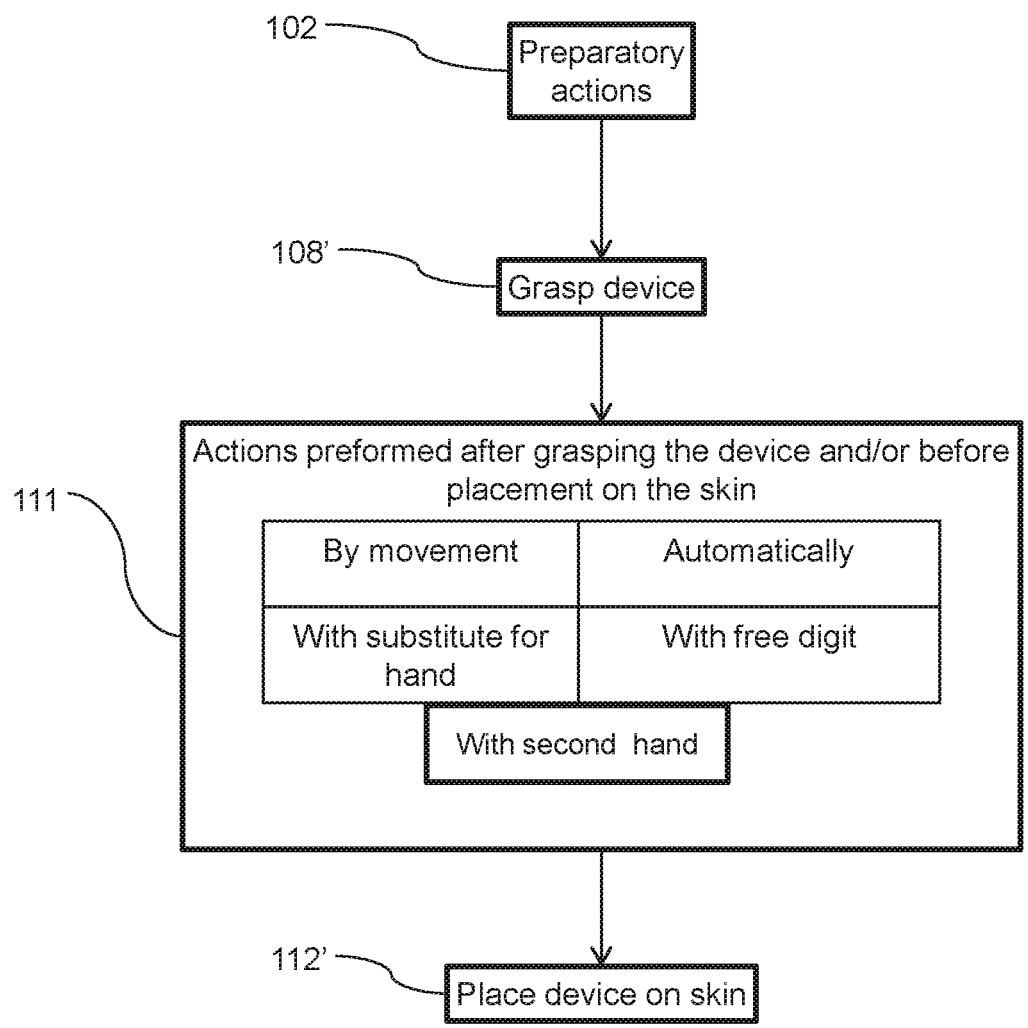
FIG. 1B is a schematic illustration of performing actions without changing a hand position on a device in accordance with an embodiment of the current invention.

FIG. 1B is a schematic diagram of an integrated drug delivery system in accordance with an embodiment of the current invention. In some embodiments, a device and/or packaging may be designed to promote proper gripping of the device. Optionally, the device is designed for integrated handling. For example, the device may be designed to allow integrated hand positioning (for example preserving a single grip on the device) during usage of the device and/or while removing the device from the packaging and/or while priming the device and/or while applying the device to a delivery site and/or while activating the device.

In some embodiments a packaging 130 may display a device 100 in a way that helps a user intuitively orient the device 100 for use. For example, a user interface 115 and/or a display 116b may be exposed to the user from the package 130. Additionally or alternatively, a handle 108a of the device 100 may be exposed to the user from the package 130. For example, handle 108a may include gripping surfaces 108a and/or 108b.

In some embodiments, the handle 108a and/or the way of grasping the device while removing the device 100 from the package 130 may facilitate integrated use of the device. For example, the grasping may integrate removing the device 100 from the package 130, preparing the device 100 and/or using the device 100. For example, handle 108a may be configured to be grasped between some fingers (for example a thumb and the three small fingers of one hand) (for example the handle may include opposing gripping surfaces). Optionally this grasping leaves a finger (for example a forefinger) of the hand free to operate a control 116a (for example a button) on a user interface 115. For example, control 116a may be placed where it is accessible to the index finger while the other fingers are holding the handle 108a. For example, this may facilitate lifting the device 100 out of the package 130 and/or activating the device 100 without changing hand position.

In some embodiments, a packaging 130 may include a guide (for example finger guides 124a and 124b) to encourage proper handling of the device 100. For example, a guide (e.g. guides 124a and/or 124b) may direct a user to position the proper fingers in the proper positions to grasp handle 108a. For example, a device 100 may include a handle 108a with opposing griping surfaces. Optionally, a first guide 124a will direct a user to place his thumb on one of the gripping surfaces and/or a second guide 124b will direct the user to place his three small fingers on the other gripping surface.

In some embodiments, a user interface may include an indicator (for example, a display 116b) which is integrated with the handle 108a. For example, display 116b may be positioned so that a user can see display 116b while holding handle 108a. For example, this may facilitate lifting device 100 out of packaging 130 and continuing to use and/or monitor the device 100 without changing hand position. For example, display 116b and/or control 116a may be placed between 0.1 to 1 cm and/or between 1 to 4 cm and/or between 4 to 10 cm in front of handle 108a.

In some embodiments, device 100 may include a delivery interface 113 configured for integration with the handling of the device for example removal from a package 130 and/or preparation of the device. For example, a delivery interface 113 may include a hypodermic needle and/or an adhesive skin contact surface. Optionally, the delivery interface 113 may be protected by a protector 109. For example, the delivery interface may be protected from contamination and/or premature activation, for example by a needle cap and/or an adhesive liner and/or a locking mechanism that prevents activation. Optionally, a priming interface 110 may be protected by packaging 130. For example, the priming interface 110 is optionally situated on a portion of the device 100 that is covered by packaging 130 until the device is removed from the packaging. For example, the priming interface may be situated opposite an exposed portion of the device 100, for example the user display 116b and/or the activation control 116a. Alternatively, the delivery interface may be protected directly by the packaging. Optionally, for example, removing the device from the packaging may prime the device.

In some embodiments, the configuration of a device 100 and/or packaging 130 may be integrated with proper preparation and/or use of the device. For example, the packaging 130 may cover over a priming interface. Optionally this may inhibit premature priming before the device 100 is removed from packaging 130. Optionally, a priming interface 110 is configured for easy priming of the device 100 while a user grasps a handle 108a of the device 100 when removing the device from the package 130. For example, the priming interface 110 may include a large priming handle that is easily pulled off while holding handle 108a with one hand. For example, the priming handle may be pulled off with the other hand and/or the teeth (for example priming the device 100 with the teeth may facilitate one handed use of the device 100). Optionally, the position of priming interface 110 may make it easy to access while holding handle 108a. For example, the priming interface 110 may be located opposite the palm of the hand holding handle 108a and/or priming interface may be distanced from the housing of the device 100, for example, to make it easy to reach priming interface 110. Optionally, the device 100 includes an activation lock. For example, the activation lock may prevent premature activation of the device (for example by preventing activation of the activation control 116a). Optionally, activation lock 112 may be blocked by a priming interface, such that it will not be unlocked until the device is primed.

In some embodiments, activation lock 112 may be part of a skin contact surface of the device 100. Optionally while a user holds handle 108a and/or works a priming interface 110, he is inhibited from unlocking activation lock 112. For example, lock 112 may be released after priming when the skin contact surface contacts an injection site.

FIG. 1A is a schematic diagram showing various ways to perform actions without changing a hand position on a device in accordance with an embodiment of the current invention. In some embodiments, a drug delivery device may be designed for integrated action from unpackaging until the end of use. For example, the device is grasped in an intuitive way and/or held in the same hand position through preparations and/or delivery of the drug. For example, actions 111 performed after initially grasping 108d the device, may be performed without needing to change a hand position on the device.

In some embodiments, various actions may be performed before grasping 108d the device. For example, the device may be powered up from outside the packaging, for example using a magnetic switch and/or through a user interface outside the package. Optionally, the package may be designed to allow access to a user interface of the device while the device remains in the package. For example, a battery isolator may protrude out of the package and/or the user may pull the battery isolator to power up the device before removing the device from the packaging. Alternatively or additionally, opening the package may trigger a preparatory action 102.

In some embodiments, when the device is initially grasped 111, it is grasped 111 with a hand position that will be used for placing 112' the device on the skin. Optionally, the packaging of the device is configured to facilitate proper grasping 111 of the device. For example, the device may be presented to the user with a gripping surface exposed to the user and/or the packaging may include spaces around the device for placement of the fingers of the user for proper grasping 108d of the device. Alternatively or additionally, the packaging may have indicators to encourage the user to properly orient and/or grasp 108d the device. For example, the package may include words and/or symbols that appear right side up only when the package is properly oriented for grasping 108d the device. For example, the package may include a base that sits on a flat surface when the device is right side up. For example, the packaging may be transparent and/or include a window through which the user can see a user interface of the device when the package is properly oriented. For example, the device may be angled toward a user when the package is properly oriented and/or angled away from the user when the package is improperly oriented. For example, the device may be supported at an angels ranging between 5 to 10 degrees of the base and/or between 10 to 30 degrees of the base and or between 30 to 45 degrees of the base and/or between 45 to 60 degrees of the base and/or between 60 to 80 degrees of the base and between 80 to 90 degrees of the base.

In some embodiments, the device is configured such that actions performed after initially grasping the device can be performed without changing the initial hand position on the device.

Optional Steps in Using a Device

Figure 2:
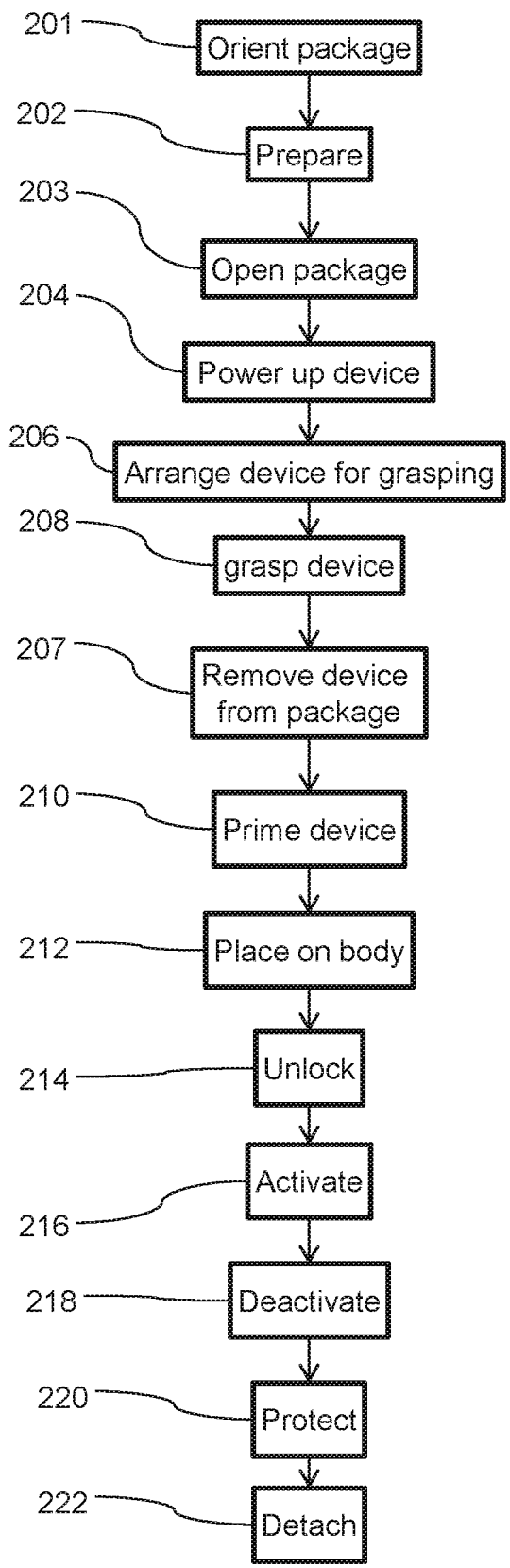
FIG. 2 is a flow chart illustration of optional steps in use of a drug delivery device in accordance with an embodiment of the current invention.

FIG. 2 is a flow chart illustration of optional steps in use of a drug delivery device in accordance with an embodiment of the current invention. Some embodiments may include all and/or some of the steps. Some embodiments may not include one of the steps. Optionally, some steps may be performed by a subject receiving a drug and/or another person, for example a personal assistant and/or a medical professional.

Figure 3:
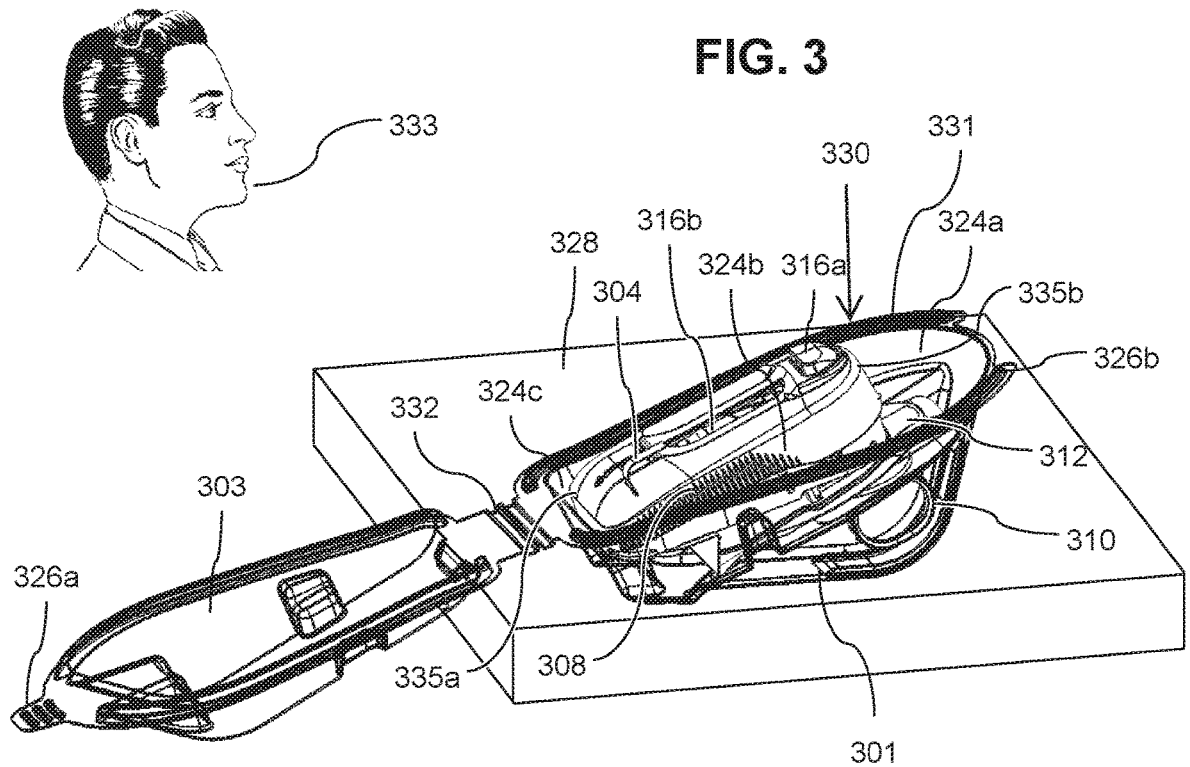
FIG. 3 is a perspective view of a drug delivery device in an open package in accordance with an embodiment of the present invention.
Figure 8:
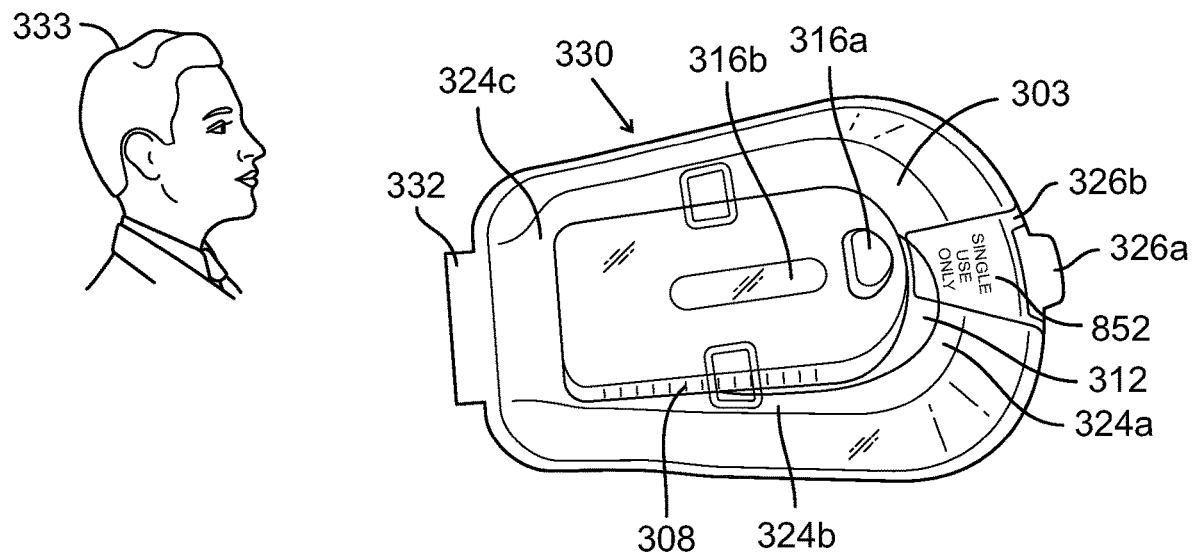
FIG. 8 is a photograph illustrating a drug delivery device in its package in accordance with an embodiment of the current invention.
Figure 9:
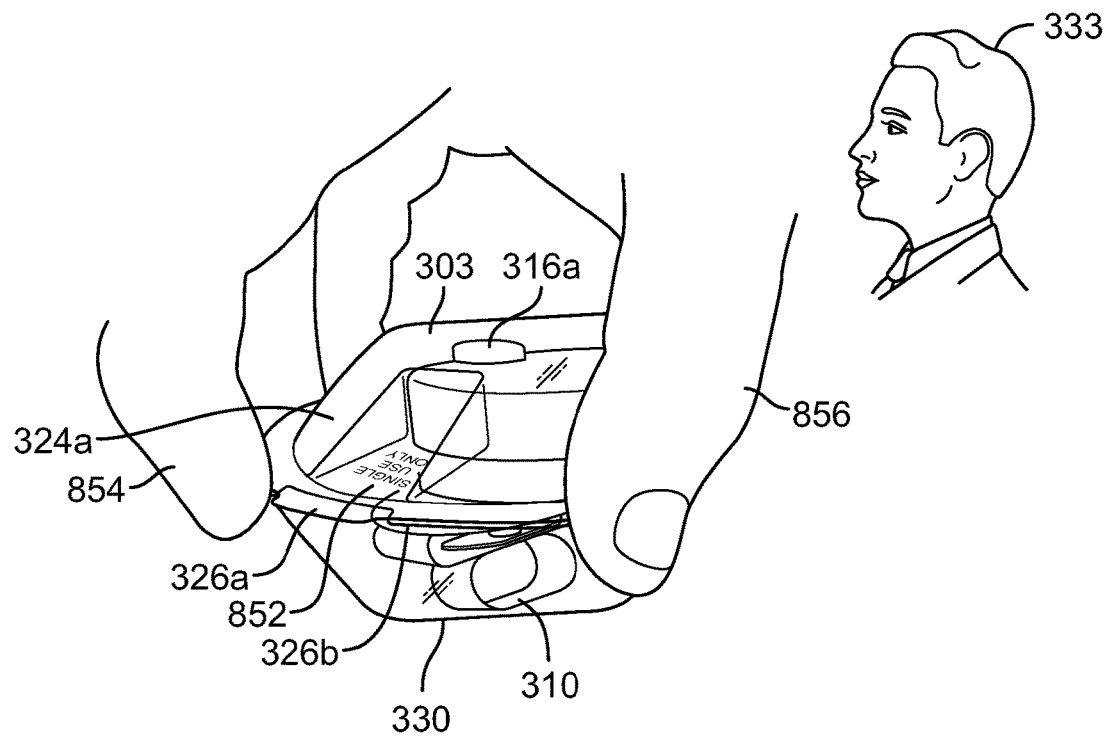
FIG. 9 is a photograph illustrating opening a package with a drug delivery device in accordance with an embodiment of the current invention.

In some embodiments, a package is oriented 201 in a particular orientation prior to opening the package. Optionally, the package may be designed to encourage a user to properly orient 201 the package (for example as illustrated in FIG. 3). For example, the package may have only one side that sits stably on a flat surface and/or may have a limited number of sides that sit stably on a flat surface. Optionally, the package may have symbols (for example letters numbers and/or pictures) whose proper orientation is obvious to a user (for example as illustrated in FIG. 8). Optionally the package may have a window or a display through which the user can see when the device is properly oriented 201. For example, the device may be visible through the package (for example as illustrated in FIG. 9). Optionally the device may be tilted such that when the package is properly oriented 201 the device is tilted towards the user (for example as illustrated in FIG. 3) and/or when the package is improperly oriented, the device is tilted away from the user. In some embodiments, an opening mechanism of the package (for example a tab and/or a pull chord and/or a release button and/or a tear tab) is easily accessible to a user when the package is properly orientated 201 and/or is less accessible when the device is not properly oriented. Optionally a preliminary action prior to opening the package will require proper orientation 201 of the user and/or packaging. For example, a user may be instructed to record a bar code on the packaging before opening the package. For example, proper orientation 201 may make the bar code visible to the user.

In some embodiments, certain activities may be prepared 202 before grasping 208 the delivery device. Optionally, activities that are difficult to perform while grasping 208 the device and/or would require changing hand position on the delivery device are preformed 202 before grasping 208 the device. Optionally preparing 202 may be before opening 203 the device packaging. Alternatively or additionally, preparing 202 may be after opening 203 the packaging, but before grasping 208 the device. For example, preparations 202 may include preparing a communication device to pair with the delivery device. For example, a code may be entered into the communication device and/or a program may be loaded onto the communication device. For example, entering code into a communication device may include manually inputting the code and/or imaging a code printed on the packaging and/or on the device. Imaging a code on the device may be performed before opening 203 the packaging (for example through a window in the packaging and/or after opening 203 the packaging).

In some embodiments, preparing 202 may include preparing the subject for the drug. For example, an injection zone on the skin may be exposed and/or cleaned, for example with an antiseptic swab. For example, preparation of the patient may be performed before opening the package. Alternatively or additionally, the device may be packaged as a kit. For example, a kit may include a patient prep kit, for example including the anti-septic swab. For example, the kit may be opened 203, the prep materials removed, patient prep performed and then the device may be grasped 208 and/or removed 207 from the package.

In some embodiments, a device may be powered up 204 before it is grasped 208 and/or before the device is removed from its packaging. For example, the delivery device may be powered up before opening a package containing the device. For example, the device may be powered up remotely, for example using a magnetic switch. Alternatively or additionally, a battery isolator of the device may protrude out of the packaging and/or the device may be powered up by pulling out the battery isolator from outside the packaging. Alternatively or additionally, the device may be powered up automatically when the packaging is opened (for example by attaching the battery isolator to a closure of the package as illustrated in for example in FIG. 3). Alternatively or additionally, the device may be powered up after opening the packaging, but before grasping 208 the device and/or removing the device from the packaging. For example, a button may be pushed on the device and/or a battery isolator may be pulled out from the device while the device is in the open package.

In some embodiments, a device may be arranged 206 for grasping. For example, the package may be designed such that the gripping surface of the device is exposed and/or positioned for easy grasping 208 (for example as illustrated in FIG. 3). Optionally, the package covers surfaces that are not used for grasping. Optionally, spaces and/or markings are provided to direct the placement of the user's hand and/or fingers for the proper grasping of the device from the package (for example as illustrated in FIG. 3).

Figure 10:
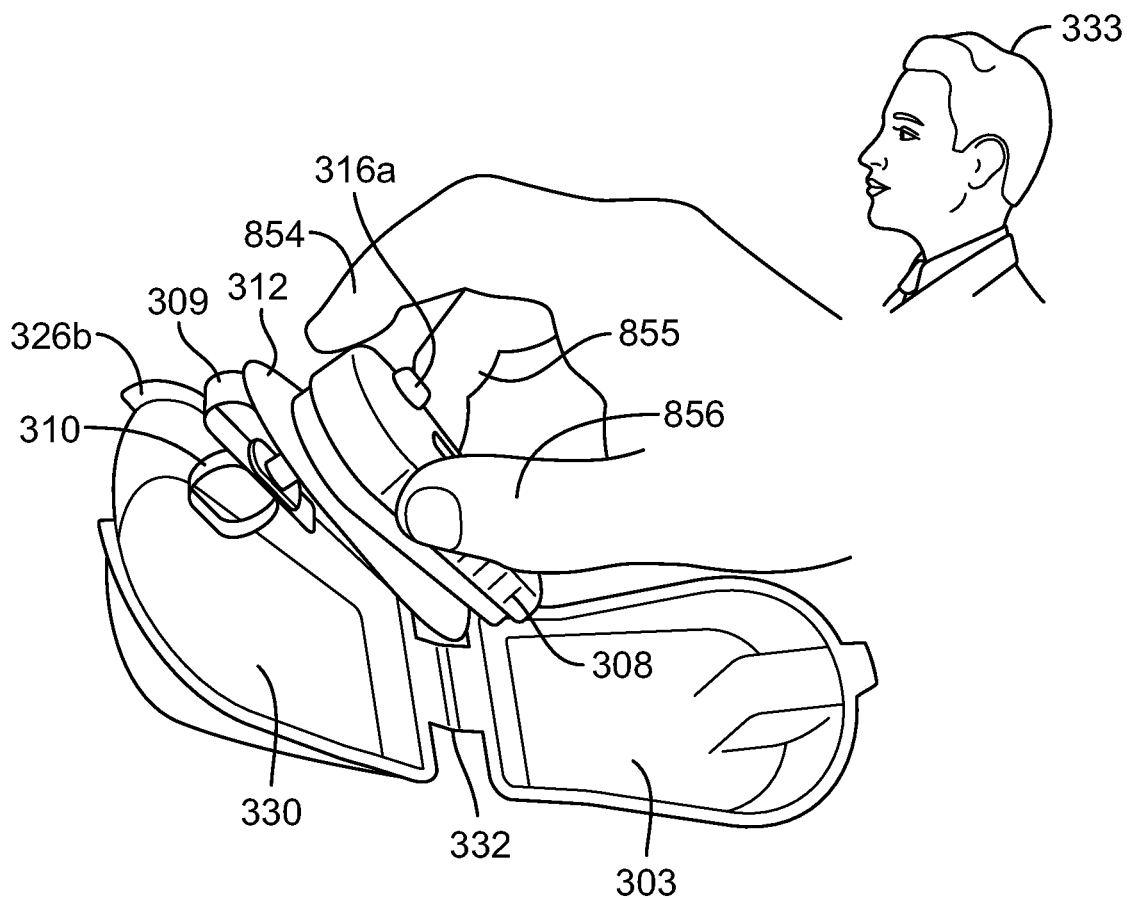
FIG. 10 is a photograph illustrating removing a drug delivery device from a package in accordance with an embodiment of the current invention.
Figure 11:
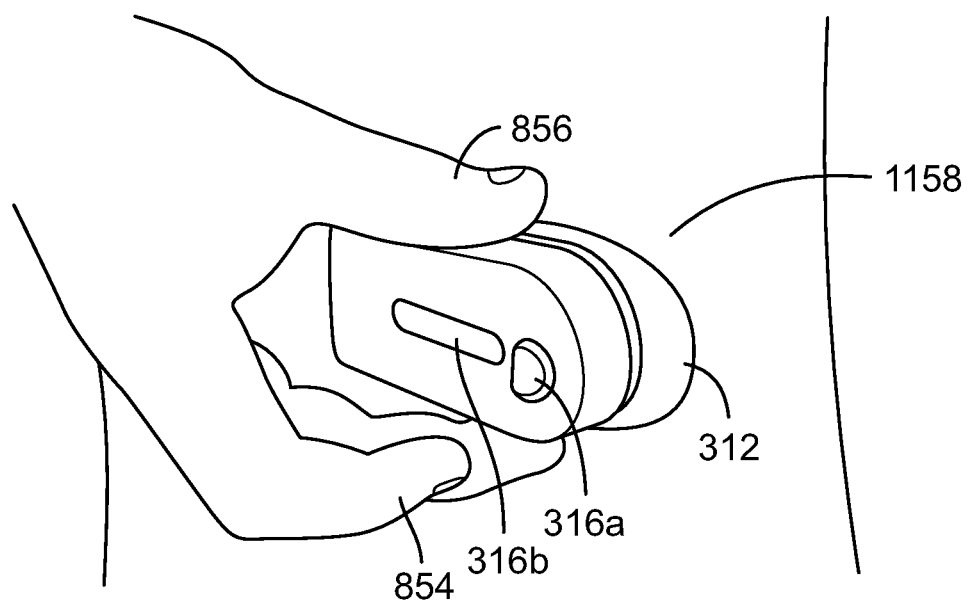
FIG. 11 is a photograph illustrating placing a drug delivery device on a body of a subject in accordance with an embodiment of the current invention.

In some embodiments, the device is grasped using a hand position that will be used for placement 212 of the device on the body of the subject and/or activation 216 of the device. Optionally, the device is removed 207 from the packaging while grasping it and/or without changing a hand position on the device (for example as illustrated in FIGS. 10 and 11).

Figure 6:
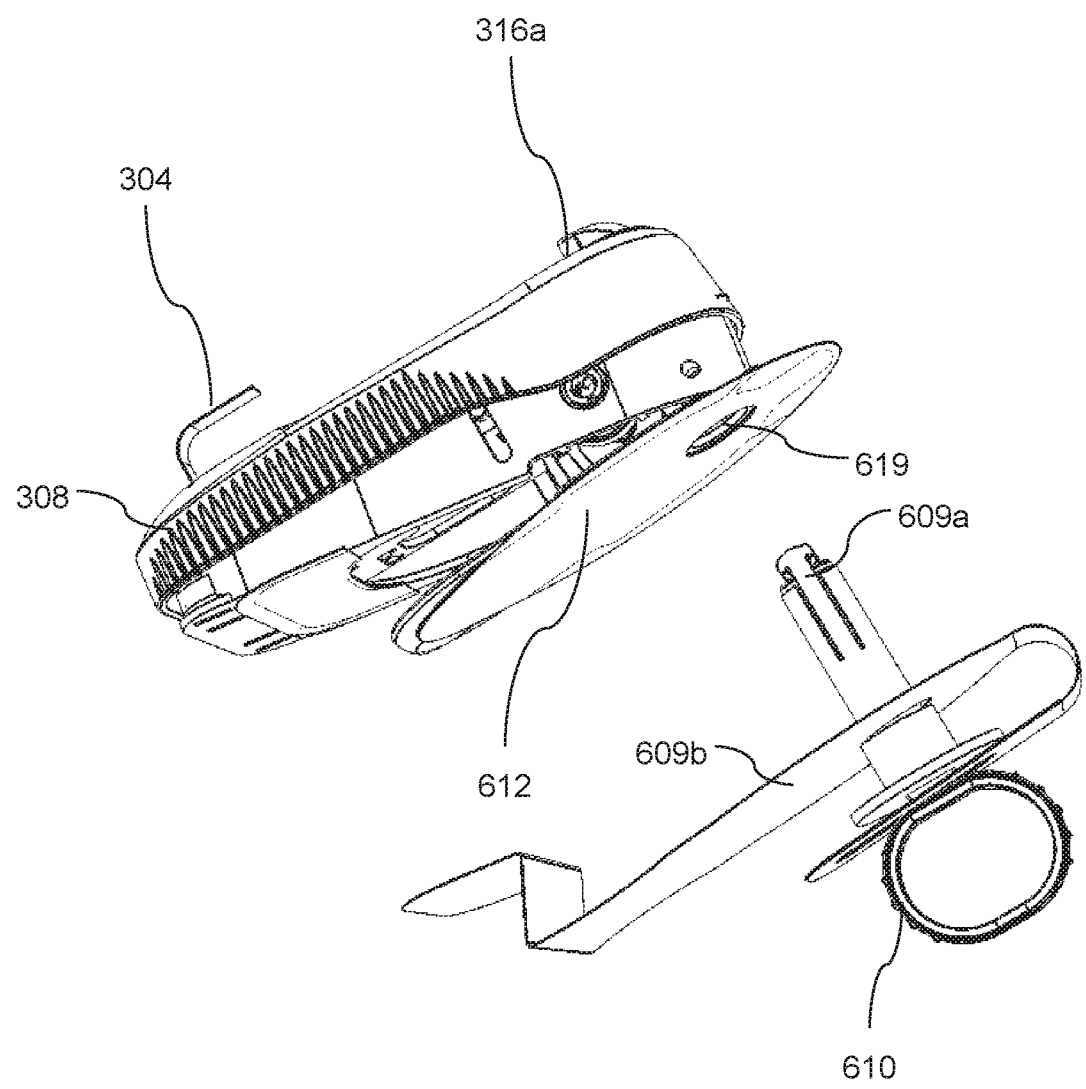
FIG. 6 is a perspective view of a priming of a delivery device by removal of a needle cover and/or adhesive liner in accordance with an embodiment of the current invention.

In some embodiments, a device is primed 210. Optionally, priming 210 is performed after removing 207 the device from the packaging without changing a hand position. Alternatively or additionally, priming may be performed before grasping 208 and/or removing 207 the device from its package. For example, priming a device may include removing a sterile cover, for example a needle cover of an injector and/or an adhesive liner (for example as illustrated in FIG. 6). In some embodiments, the sterile cover protects sterility of a delivery interface of the device (for example sterile parts and/or surfaces of the interface. Optionally, the external packaging may not need to preserve sterility. For example, non-sterile packaging may be less bulky, easier to open and/or easier to orient than sterile packaging.

In some embodiments, a delivery device may be placed 212 on a skin of a subject. Optionally, the hand position used to grasp 208 the device and/or remove 207 the device from its packaging is not changed and/or is also used for placing 212 the device onto the injection site (for example as illustrated in FIGS. 10 and 11).

In some embodiments, a drug delivery device may be unlocked 214 while the device is held using the same hand position as when grasped 208 from the packaging. For example, the delivery device may include a safety feature to prevent needle extension and/or drug delivery unless certain steps are performed in a proper order to unlock 214 the device. For example, the unlocking may be triggered by certain movements of the device (using for example an inertial sensor) and/or by proximity to an injection site (for example using a skin sensor to unlock the device when it is placed 212 on the injection site (for example as illustrated in FIG. 6)).

In some embodiments, a device may be activated 216 while the device is being grasped 208 by the user. Optionally, the device may be grasped 208 by some of the digits of a user's hand and/or activated 216 using another, free digit of the same hand. For example, the free digit may be used to operate a user interface. For example, the device may be grasped 208 between a thumb and one or more of the middle finger, ring finger and/or pinky while the index finger remains free to operate a user interface and/or to activate 216 the device (for example as illustrated in FIG. 11). For example, the device may be grasped by one or more of the middle finger, ring finger, pinky and the index finger while the thumb remains free to operate a user interface and/or to activate 216 the device. For example, the device may be grasped 208 by one or more of the middle finger, ring finger, and pinky while the index finger remains free to operate a user interface and/or to activate 216 the device (for example as illustrated in FIG. 4). Alternatively or additionally, the device may be activated 216 by a more gross activity such as pushing the device against the skin with the entire hand and/or by manipulation of the group of digits grasping the device (for example twisting a grip and/or pushing the grip toward the skin and/or squeezing the grip and/or squeezing the device). Alternatively or additionally, once the device is placed 212 on the skin, the user may change his hand position. For example, the device may be adhered to the body and then the user may remove his hand and/or activate 216 the device.

In some embodiments, the user interface of a device may include a button for activating the device. Alternatively or additionally, the user interface may include a display (for example a screen and/or a light and/or a window) in a position, which encourages the user to hold the device with the display visible (for example directing his grasping 208 of the device not to cover the display). Optionally, orienting 201 the package and/or device may be arranged to cause the display to face the user's eyes.

In some embodiments, the device may be deactivated 218. For example, a device may automatically deactivate 218 when it finishes delivering a prescribed dose of the medicine and/or when a fault occurs in the delivery. Alternatively or additionally, the device may automatically deactivate 218 when it is detached 222 from the skin. Alternatively or additionally, a user may manually deactivate the device. Optionally, deactivation 218 may occur while the user is grasping the device with the same hand position as when he first grasped 208 the device from its packaging. For example, the user may pull the device off the skin while grasping the device with the same hand position as when he first grasped 208 the device. For example, the user may control a user interface while grasping the device with the same hand position as when he first grasped 208 the device.

In some embodiments, a device may be detached 222 from the skin. Optionally detachment 222 is after deactivation 218. Alternatively or additionally, detachment 222 is before deactivation 218. In some embodiments, a device may be protected 220 (for example by shielding or retracting a needle) at the end of delivery and/or when the device is deactivated 218 and/or when the device is detached 222 and/or in response to a user action.

a given embodiment may include some or all may be preformed before gripping and/or while gripping without changing grip Exemplary Embodiments of a Device and/or Packaging FIG. 3 is a perspective view of presenting a drug delivery device to a user in an open package in accordance with an embodiment of the present invention. Optionally, the package is configured to be opened with one hand. Optionally, the package is configured to encourage proper orientation. Optionally, the package is configured to present the device for proper grasping. Optionally, the device is designed for handling from opening the package to activation with a single hand position. In some embodiments, preparatory actions may be performed before opening the package and/or before grasping the device.

In some embodiments, a package 330 includes a one handed user interface. For example, the user interface may include tabs 326a and 326b on a closure 303 and a body 331 of the package respectively. Optionally, closure 303 is connected to body 331 by a hinge 332. FIG. 3 shows the package 330 in an open state. In some embodiments, in a closed state, closure 303 is rotated around hinge 332 until tab 326a of closure 303 is located beside tab 326b of body 331. Optionally, before opening package 330, package 330 is placed on a flat surface 328. In some embodiments, a package includes indicators to help a user recognize a vertical orientation (e.g. which side of the package should be oriented downward for example as illustrated in FIG. 8). For example, the package 330 is shaped to help a user 333 recognize that the base 301 should be oriented downward. For example, the base 301 is flat and/or sits stability on a flat surface 328. Optionally, other surfaces of the package 330 are curved and/or angled in such a way that a user can intuitively recognize that they do not sit properly on a surface 328 and/or are not the base. Alternatively or additionally, symbols (for example arrows) may be printed on package 330 indicating which side goes down. Alternatively or additionally, a label may be positioned such that it is visible, legible and/or properly oriented with respect to the user when the package 330 is properly oriented with respect to the user (for example as illustrated by label 852 of FIGS. 8 and 9).

In some embodiments, while the package 330 is still closed, package 330 is oriented in the horizontal plane with hinge 332 oriented towards user 333 (An approximate position and/or orientation of user 333 is shown schematically in the FIG. 3). A closed package is shown, for example, in FIGS. 8 and 9 with a schematic representation of user 333 position and/or tabs 326a and 326b opposite user 333. A package optionally includes an indicator of horizontal orientation. For example, horizontal orientation may be indicated by letters and/or symbols that appear right side up when the device is properly oriented. Alternatively or additionally, the delivery device may be visible to user 333 through package 330 (for example, package 330 may include a window and/or package 330 may be transparent for example as illustrated in FIG. 9). For example, when package 330 is properly oriented in the horizontal plane with respect to user 333, the delivery device may be angled with a face towards the face of user 333 (for example when package 330 is properly oriented, the end 335a of the delivery device near user 333 may be angled downward and/or the end 335b far from user 333 may be angled upward).

By pushing tab 326a with one finger and pushing with another finger in an opposite direction on tab 326b, a user 333 opens package 330 with one hand (for example as illustrated in FIG. 9). For example, package 330 may be a non-sterile package. Optionally, there is no need to break a sterile seal to open package 330.

In some embodiments, a battery isolator 304 is attached to closure 303 of package 330. For example, when the package 330 is opened, battery isolator 304 is pulled by closure 303 out of the delivery device thereby powering up the device. Alternatively or additionally, a battery isolator may protrude from a slit in the package 330 and/or the device may be powered up by a remote control. For example, the device may be powered up before opening the package. Alternatively or additionally, the battery isolator 304 may not be connected to closure 303. Alternatively or additionally, the device may be powered up after opening package 330 and/or before removing the delivery device from the body 331 of package 330. For example, battery isolator may be pulled out of the device directly by the user, powering up the device after opening package 330. Alternatively or additionally, the device may be powered up after removal of the device from the package body 331. For example, a battery isolator may be pulled out while the device is be grasped by the user and/or after the device is removed from the body 331 of package 330. For example, the battery isolator may be connected to a handle (for example needle cover remover handle 310) that is removed while the device is being grasped.

In some embodiments, a package is configured to facilitate a user grasping and/or removing a drug delivery device (for example a patch injector) from the package in a position ready for use of the device (for example placement on the skin of a subject). For example, when base 301 of package 330 rests on a horizontal flat surface 328 and/or when package 330 is opened, the delivery device is positioned in package body 331 with a skin contact surface facing into package body 331. Optionally, when user 333 grasps the device from the package base 331, his hand does not block skin contact surface 312. For example, the package 330 includes gaps 324a, 324b and/or 324c is configured to encourage proper positioning of fingers around the device.

In some embodiments, a location on the device which is not intended to be grasped by the user is optionally sunk into a package and/or blocked by a package. For example, exemplary device of FIG. 4 is packaged with the tight space (of for example less than 1 cm and/or less than 0.1 cm) between a rear end 335a of the device and the rear wall of the package 330. This packaging inhibits improper positioning of fingers (e.g. behind the device).

In some embodiments, a location which is intended to be grasped by the user optionally extends out of the package and/or has a space between it and the package. For example, the exemplary device of FIG. 4 is packaged with a space (of for example greater than 1 cm and/or greater than 0.1 cm) between a gripping surface 308 of the device and the wall of the package 330. This packaging encourages proper positioning of fingers (e.g. bend, gripping surface 308). Optionally, a location for placing a thumb (for example towards the front of the exemplary device of FIGS. 3 and/or 11) has more space than a location which is meant to be grabbed with a small finger (for example the back side gripping surface 308 of the exemplary device of FIGS. 3 and/or 11). For example, the area for a thumb may be larger by a factor of between 1 to 1.3 and/or between 1.3 to 1.6 and/or between 1.6 to 2 and/or between 2 to 5.

In some embodiments, a gripping surface is designed to encourage easy grasping. For example, the surface 308 is textured to encourage grasping (for example surface 308 is rough). Optionally a gripping surface is directed for easy grasping. For example, surface 308 is tilted slightly away from user 333 and/or is situated opposite a second surface for grasping the device from two sides. Alternatively or additionally, a surface not meant to be grasped may be configured to discourage grasping. For example, the front end the exemplary device of FIGS. 3 and 11 is smooth and/or convex and/or not close to an opposing surface that is easily grasped. Optionally, a gripping surface is at an angle ranging between 5 to 10 degrees, and/or between 10 to 30 degrees and/or between 30 to 50 degrees and/or between 50 to 80 degrees and/or between 80 to 85 degrees of horizontal and/or of the base of the device.

In some embodiments, a user interface is located for activation with a free digit. For example, an activation button 316a is placed to be accessible to an index finger of user 333 while user 333 is grasping the surface 308 between his other fingers and his thumb (for example as illustrated in FIG. 11). In some embodiments, the use of a free digit on a user interface may allow a user to simultaneously hold and/or activate a device using one hand. Optionally the device includes an indicator. For example, the device may include a status window 316b. For example, the status window may show the drug reservoir and/or a plunger position and/or a coded status indicator (for example an LED). Optionally, an indicator 316b (for example a window exposing the medicine reservoir of the device) is visible to the user 333 when the device is properly oriented and/or the package is opened and/or while the user is grasping the device. Additionally or alternatively, the indicator 316b is visible when the packaging is closed, for example, through a transparent portion of closure 303 (for example as illustrated in FIG. 8).

In some embodiments, a user interface may be configured for activation with a gross action and/or a limb and/or an object other than a user's hand. For example, a control 310 of the device may be configured to be anchored by an object other than a user's hands, for example between the teeth and/or to hook over a stationary object (for example a coat hook and/or door handle). For example, a drug delivery device may be primed by removing a needle cover and/or an adhesive liner 309 (for example needle cover 609a and/or adhesive liner 609b for example as illustrated in FIG. 6). Optionally, the control 310 includes a large ring. The ring optionally is anchored while the user pulls the device away from the ring to remove the needle cover and/or adhesive protector. Alternatively or additionally, an action may be triggered by a gross motor activity for example pushing the device against a surface. For example, a safety latch may be connected to a skin contact surface 312 of a delivery device. When the skin contact surface 312 is pushed against the skin of a subject, the safety latch optionally acts as a skin sensor and/or unlocks a needle insertion mechanism. Pushing skin contact surface 312 against the skin of the subject (e.g. the injection zone) is optionally performed while using the hand to hold the device without removing ones fingers from the device.

Figure 4A:
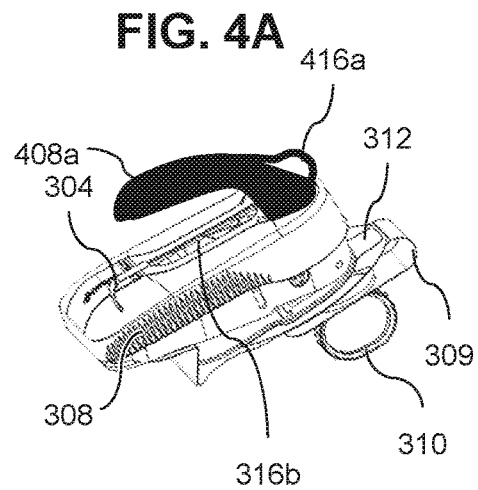
FIGS. 4A and 4B are a perspective views of an alternative drug delivery devices in accordance with embodiments of the present invention.

FIG. 4A is a perspective view of an alternative drug delivery device in accordance with an embodiment of the present invention. For example, the device of FIG. 4A includes a grip 408a extending away from the device and a button 416a configured to be pushed with a thumb while holding the bar 408a with the fingers (for example similar to the steam button of a steam iron). Optionally. grip 408a can be removed from the delivery device after the device is adhered to the skin. Alternatively or additionally, a delivery device may include a pistol grip and/or a trigger.

Figure 4B:
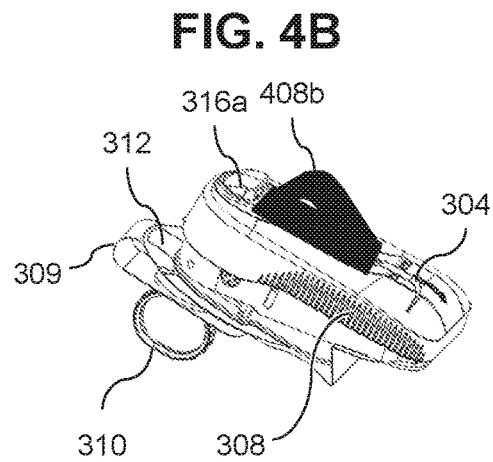

FIG. 4B is a perspective view of an alternative drug delivery device in accordance with an embodiment of the present invention. For example, the device of FIG. 4A has a hand strap 408b attached to a dorsal surface of the device (e.g. opposite skin contact surface 312). Optionally, the strap 408b is positioned such that while the user's hand is held by the strap, his thumb is free and/or positioned to push button 316a.

Patch Injector

Figure 5:
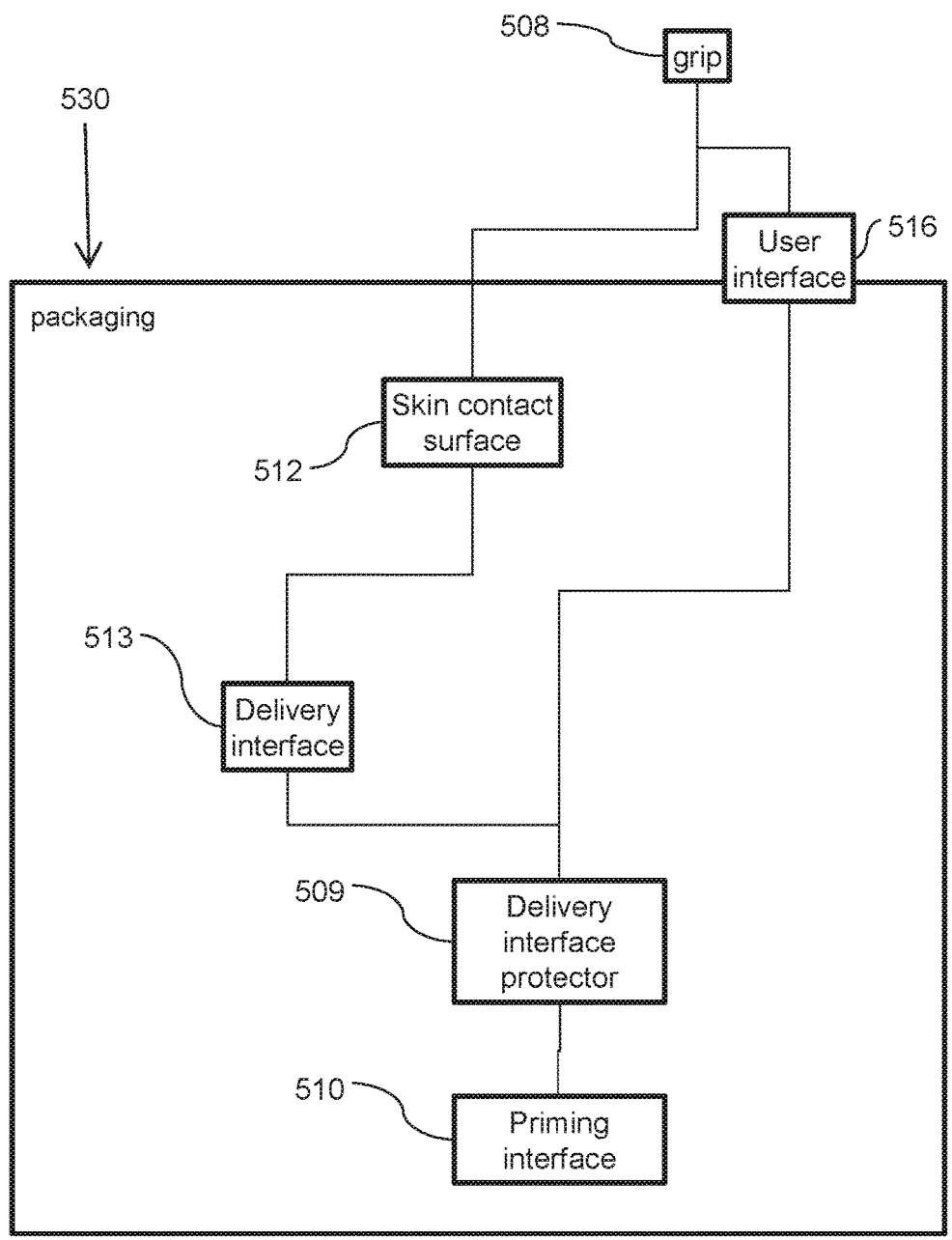
FIG. 5 is a block diagram of a drug delivery device in accordance with an embodiment of the current invention.

FIG. 5 is a block diagram illustration of a drug delivery device in accordance with an embodiment of the present invention. In some embodiments, a package 530 is configured to protect a delivery device during transport and/or to present the device to a user in a way that integrates unpacking, grasping, and/or using the device. Optionally, the device includes a grip and/or control interface that allows removal from the packaging, preparation of the device, and/or use of the device in a coordinated fashion, for example, with a single hand and/or without changing a hand position grasping the device. Optionally, the packaging and/or the device are bilateral and/or can be used with either hand. In some embodiments, a package may protect sterility of a device. Alternatively or additionally, a package may not protect sterility (for example, the delivery device may include its own sterility protection, for example including a needle cover and/or an adhesive liner for example as illustrated in FIG. 6).

Figure 7:
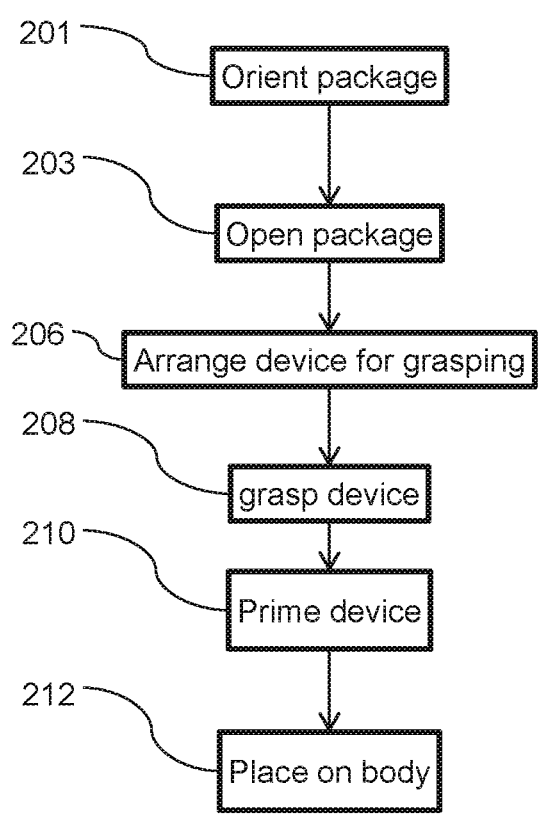
FIG. 7 is a flow chart illustration of a method of priming a drug delivery device in accordance with an embodiment of the present invention.

In some embodiments, the delivery device includes a grip 508 (for example including a gripping surface). Optionally, grip 508 is exposed to a user while the device is still in the package (for example after opening the package). Optionally, the device includes a user interface 516. For example, the user interface 516 may include an indicator by which a user can determine a status of the device and/or a control by which the user may control the device. Optionally, the user interface 516 is configured for use while the user is grasping grip 508. For example, while the user is grasping grip 508, an indicator (for example a display and/or a window showing a drug reservoir) may be visible to the user. For example, while the user is grasping grip 508, a control (for example an activation button) may be accessible to the user (for example using a free digit of the hand that is grasping grip 508 and/or by another means and/or using another object. Optionally, the indicator may be exposed to the user while the device is in the package. For example, a status window may be visible through a transparent package 530 (for example as illustrated in FIG. 7) and/or through a window in the package 530.

In some embodiments, a drug delivery device will include a delivery interface 513. For example, a drug may be delivered at a delivery site including, for example, a portion of the skin of a subject. Optionally, the interface 513 includes a skin contact surface 512 (for example as illustrated in FIG. 6). For example, the skin contact surface 512 may include an adhesive. For example, the interface 513 may include a hypodermic needle. In some embodiments, the delivery interface 513 is protected and/or covered by the package 530. For example, the interface 513 may be protected from damage during transport and/or handling. For example, a user may be inhibited from grasping the interface 513 and/or blocking the interface 513 after opening the package 530 and/or before grasping grip 508.

In some embodiments, a drug delivery device will include a delivery interface protector 509. For example, a delivery interface protector 509 may include a needle cap (for example cap 609a as illustrated in FIG. 6). For example, a delivery interface protector 509 may include an adhesive cover (for example adhesive liner 609b as illustrated in FIG. 6). For example, the protector 509 may separate between a sterile portion of the device and a non-sterile portion of the device. For example, a delivery interface may be retained sterile and/or sealed away from a non-sterile portion of the device. For example, a user interface of the device and/or an external surface and/or a non-sterile package may be separate and/or sealed away from the sterile portion by protector 509. In some embodiments, delivery interface protector 509 is protected and/or covered by package 530. For example, the protector 509 may be protected from damage during transport and/or handling. For example, the protector 509 may be protected from separation of the protector 509 from the interface 513 before the device has been removed from the packaging 530.

In some embodiments, a delivery device may include a priming interface 510. Optionally, priming includes removing the delivery interface protector 509. For example, a priming interface 510 may include a handle connected to the protector 509 and configured for use to remove the protector 509 from the delivery interface 513 (for example a handle 610 which is used to remove needle cover 609a and/or an adhesive liner 609b as illustrated in FIG. 6). Alternatively, or additionally, the delivery interface protector 509 may be configured to separate from deliver interface 513 automatically. For example, the protector 509 may be connected to the packaging 530 such that pulling the device from the packaging 530 separates protector 509 from delivery interface 513 and/or primes the delivery device. In some embodiments, the protector 509 is protected and/or covered by the package 530. For example, the interface 510 may be protected from damage during transport and/or handling. For example, the interface 510 may be inhibited from separating the protector 509 from the interface 513 while the device is in the packaging 530. For example, the interface 510 may be protected to inhibit a user from priming the device prematurely. Optionally, when the user grabs the delivery device from the package, the interface 510 will be exposed facilitating priming of the device before placement on the body of the subject and/or before delivery.

In some embodiments, the packaging may expose a user interface when the user first encounters the device. For example, the user interface may be viewable through a window in the packaging before the packaging is opened and/or the packaging may be designed such that when the package is opened the user interface faces the user and/or the device may be placed in the packaging such that when the device is unpacked (for example, when it is removed from the packaging) the user interface is exposed to the user. Optionally, the user interface may include familiar operational features. For example, features may include a manually operated feature (for example a pull tab, a pull ring, and/or a button) and/or a display (for example a screen and/or a light and/or a window). The position of the feature may encourage the user to hold the device with the feature operable and/or with the display visible (for example directing his grasping of the device not to cover up a feature and/or orienting the device such that the feature faces the user's limbs and/or eyes).

In some embodiments, a user may prepare a device for use. For example, preparing a device for use may include removing a sterile needle cap and/or removing a protective liner from a skin contact surface. Optionally, multiple components of the device may be interconnected and/or prepared together. For example, a protective needle cap and an adhesive liner may be connected to a single handle, for example a pull ring. Pulling the pull ring optionally removes the cap and the liner together. Alternatively or additionally, preparing one part may start a process that enables and/or causes preparing of another part.

Exemplary Steps in use of a Drug Delivery Device

FIG. 6 is a perspective view of a priming of a delivery device in accordance with an embodiment of the current invention. Optionally, priming includes exposing a delivery interface of the device. For example, the interface may be exposed by removing an interface protector. The protector, optionally, protects sterility of the delivery interface and/or protects the delivery interface from dirt and/or protects the delivery interface from physical damage. For example, a delivery interface may include a hypodermic needle and/or an adhesive skin contact surface 612. Optionally, surface 612 may include an activation lock. For example, when surface 612 is pushed against an injection site, it may enable activation of the device. Optionally, the interface protector may include a needle cover 609a and/or an adhesive liner 609b. In some embodiments, a delivery device is primed by removing the protector and/or exposing the delivery interface. Optionally, the protector may include a handle 610. For example, a handle 610 may include an anchor suitable to immobilize a part of the protector. For example a handle that can be grasped with the teeth and/or a hook and/or a ring suitable for fixing to a stationary object (for example a coat hook). Alternatively or additionally, the device may have a release switch to prime the device and/or remove the needle cover and/or the adhesive liner. For example, the release switch may be worked using a free digit of a hand holding a grip of the device.

In some embodiments, priming may include removing a sterility protector of a device. For example, a needle cover and/or an adhesive liner may preserve sterility of the device (for example the cover may preserve sterility of a needle and/or a delivery interface). For example, protecting sterility with a cover may facilitate packaging the device in a non-sterile package. Optionally, before activation of a device, a tip of a needle of the device is concealed and/or shielded behind a skin contact surface 612. For example, the surface 612 may include a needle opening 619. Optionally, a needle cover fits through the opening 619 and/or protects the needle tip and/or preserves sterility of the needle tip. Optionally, the cover 609a may seal off the needle tip from other portions of the delivery device. For example, the outer surface of the device and/or inner portions of the device and/or the user interface of the device may be non-sterile while the cover 609a separates the non-sterile portions of the device from the needle tip. When the device is activated, the needle tip optionally protrudes out from the opening 619 into the skin of a subject and/or a drug is injected through the needle into the subject.

In some embodiments, a handle 610 may extend between 1 to 2 cm from the delivery interface and/or between 2 to 4 cm and/or between 4 to 8 cm and/or may have an opening that can be slipped over a projection of diameter between 1 to 2 cm and/or between 2 to 4 cm and/or between 4 to 8 cm. Optionally, a handle 610 will have a thickness between 0.5 to 2 cm. Optionally, a handle 610 includes a high friction surface and/or a soft surface (for example between 30 shore 00 to 0 shore A and/or between 0 shore A to 20 shore A and/or between 20 shore A to 40 shore A and/or between 40 shore A to 100 shore A).

FIG. 7 is a flow chart illustration of a method of priming a drug delivery device in accordance with an embodiment of the present invention. For example, a device may be oriented 201 for access to the user. Optionally, the device is oriented for easy opening of the package. Alternatively or additionally, the device is oriented before opening 203 a packaging for easy simple access to the device once the package is opened. Optionally, a package is opened 203 exposing the device arranged 206 for grasping (for example with a gripping surface exposed to the user). The user optionally grasps 208 the device from the package with a hand position that will continue to be used for placement of the device on a delivery site.

In some embodiments, while holding the device in a hand position ready for placement on the skin, the user primes 210 the device. For example, priming 210 may include removing a delivery interface protector. For example, a handle of the protector may be anchored (for example by connecting to an object and/or by grasping between the teeth) and pulled off the device by moving the device away from the object to pull the delivery interface protector away from the delivery interface, exposing the delivery interface. The exposed delivery interface is optionally placed 212 onto an injection site.

Optionally, a user prepares a patch injector for use by simple intuitive steps. Optionally, multiple steps may be performed simultaneously and/or sequentially while grasping the device in a single hand position.

In some embodiments, the device may be designed for grasping from the packaging in a position used for priming and/or activating the device and/or placing the device on the skin of a subject. For example, the device may be packaged in a way that presents the device in a proper orientation when the device is unpacked. For example, when the packaging is open, the device may be presented to the user in a way that encourages grasping of the device in the proper hand position for further steps in deployment and/or use of the device. For example, a gripping surface and/or a surface opposite the skin contact surface of the device may be presented to the user upon opening the packaging. Other surfaces may be hidden or blocked. For example, a skin contact surface may be oriented opposite the user. For example, a surface that is not to be grasped may be sunken into and/or covered by the packaging.

State Diagram of an Injector

FIG. 8 is a photograph illustrating a drug delivery device in its package in accordance with an embodiment of the current invention. For example, the closed package is shown oriented with respect to a user 333 ready for opening and/or removal of the delivery device. Optionally, a label 852 is oriented for right side up for reading by the user when the package is properly oriented. Optionally, the package is transparent. For example, when the device is properly oriented, the user interface (including for example the activation button 316a and/or an indicator 316b) of the device is visible through the closure 303 of the packaging.

FIG. 9 is a photograph illustrating opening a package of a drug delivery device in accordance with an embodiment of the current invention. For example, a user 333 stands behind the hinge of closure 303. Using a forefinger 854 of one hand, user 333 pulls up on the tab 326a of the closure 303 while creating a counter force, for example, by pushing down on the tab 326b of the body 331 with a thumb 856 of the same hand to open the package.

In some embodiments, a cover separates from a package with a small movement. For example, the package may include a safety seal that opens with a small movement. Optionally, the seal may break by a movement small enough to be applied by one finger while holding the device with another finger. For example, while a thumb 856 holds down the base 330 an index finger 854 pushes up cover 303. For example, after a small movement (e.g. of between 0.1 to 0.5 cm and/or between 0.5 to 2 cm and/or between 2 to 10 cm) a cover may be separated. For example, the label 852 may rip when the cover 303 is moved 0.5 cm from the base 330. Optionally, packaging may be designed to remain stable while opening. For example, the packaging may have a large footprint sitting on a flat surface. For example, the footprint may be between 2 to 5 cm and/or between 5 to 20 cm. For example, the footprint may be 1.2 to 2 and/or 2 to 10 times the size of the device. Optionally, the center of gravity of the package will be low, for example between 0 to 1 cm and/or between 1 to 2 cm and/or between 2 to 5 cm. Optionally, the center of gravity of the package will be between 0 to 10% of the width of its base and/or between 10 to 40% of the width of its the base and/or between 40 to 80% of the width of its base. For example, the device may have a stiff cover and/or the cover may not be adhered to the base over a large space. For example, in some embodiments, a package may not have an adhered Tyvek sealing line to a pliable cover that requires a long movement to separate.

FIG. 10 is a photograph illustrating removing a drug delivery device from a package in accordance with an embodiment of the current invention. Optionally, the user 333 remains in the same position (e.g. behind hinge 332) as he stood during opening of the package. Optionally, the device is grasped between the thumb 856 and the minor fingers 855 (i.e. all the fingers except the index finger) of one hand of the user 333. The forefinger 854 remains free and/or may help steady the device. Indicator 316b is optionally facing the eyes of user 333 and exposed for viewing.

In some embodiments, the user interface includes an object configured to be pulled with the teeth. For example, the handle 310 may be designed to hold with the teeth. Alternatively or additionally, the handle 310 may be designed to easily be pulled off while holding the handle 310 with the teeth. For example, the gripping surface 308 may be designed so that the handle 310 can be easily brought to the mouth while gripping the device and/or so that the device can easily be pulled away from the handle 310 in a direction to remove the needle cover 609a. For example, the gripping surfaces 308 may be such that when holding surfaces 308 between the fingers, the palm of the hand is opposite the adhesive surface and/or substantially perpendicular to the direction of pulling of the needle cover 609a (for example at an angle between the palm of the hand and the axis of the needle may range between 90 to 80 degrees and/or between 80 to 60 degrees and/or between 60 to 30 degrees and/or between 30 to 180 degrees to the axis of a needle and/or needle cap 609a). Optionally, the cap 609a is configured to be removed with a low force. For example, the force may be low enough so as to not damage the teeth while being pulled. For example, the pulling force may be between 0.01 to 0.2 kg force and/or between 0.2 to 0.5 kg and/or between 0.5 to 1 kg force. Optionally, a pulling handle will be distanced away from a surface enough to grasp with a mouth. For example, the handle may be a distance between 0.2 to 1 cm and/or between 1 to 3 cm and/or between 3 to 10 cm from the contact surface 612. Optionally, the handle 610 is wide enough to be easily fit into the mouth and/or be bit by the teeth, for example between 0.1 to 1 cm and/or between 1 to 3 cm and/or between 3 to 8 cm. Optionally, the handle 610 is thick enough to be easily held in the teeth, for example between 0.1 and 0.3 cm and/or between 0.3 to 0.8 cm and/or between 0.8 to 2 cm.

FIG. 11 is a photograph illustrating placing a drug delivery device on a body of a subject in accordance with an embodiment of the current invention. The device is optionally grasped with the same hand position as was used when removing the device from its packaging (for example, as illustrated in FIG. 10 between the thumb 856 and minor fingers 855). Optionally, one digit (for example, forefinger 854) remains free. For example, a user interface (activation button 316a) is positioned between the gripping surface 308 and offset towards the front of the device between 1 and 5 cm. For example, the button 316a is in a position easily reached by the free digit 854. For example, once the device is positioned on a delivery site 1158, the button 316a is pushed to by the free digit 854 to activate delivery. Optionally, the button 316a is pushed towards the delivery site 1158. Optionally, the skin of the injection site 1158 provides a counter force against which the button 316a is pushed. Alternatively or additionally, the device includes a safety lock which is unlocked by pushing a skin sensor (for example attached to skin contact surface 312) against the injection site 1158. For example, pushing a skin contact surface 312 against the injection site 1158 is done while grasping the device without changing the hand position (for example as illustrated in FIGS. 10 and 11 between thumb 856 and minor fingers 855).

States of an Delivery Device

Figure 12:
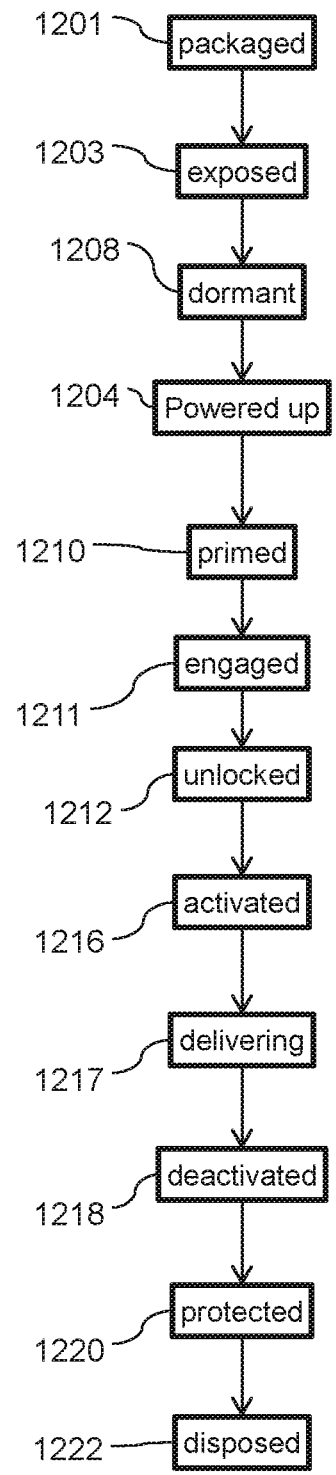
FIG. 12 is a state diagram illustration of an injector in accordance with an embodiment of the present invention.

FIG. 12 is a state diagram illustration of a delivery device in accordance with an embodiment of the present invention. In some embodiments, a device may include only some and/or all of the listed optional states. In some embodiments, the device is supplied to a user packaged 1201 in a package (for example, as illustrated in FIG. 8 and/or FIG. 9). Optionally, the package is opened to place the device in an exposed 1203 state (for example, as illustrated in FIG. 3). In some embodiments, the device remains dormant 1208 until the device is powered up to a powered up 1204 state for example by connection to a power supply, for example, by removal of a battery isolator. In some embodiments, the device is powered up before and/or during and/or after opening of the packaging. In some embodiments, the device is powered up after removal from the packaging. In some embodiments, a user may prime the device (for example by removing a protective cover, for example, a needle cover and/or an adhesive liner) to place the device in a primed 1210 state. In some embodiments, priming the device activates a skin sensor. Optionally, the primed 1210 state may be called a skin detection state (e.g., wherein the device is ready to sense a skin of a subject). In some embodiments, priming may occur automatically upon removal of the device from a packaging and/or upon opening of the package (for example, previous to and/or simultaneous to powering up the device). Optionally, the device in the primed 1210 state is attached to a subject to place it in an engaged 1211 state, for example, as illustrated in FIG. 11. Optionally, the engaged 1211 device is unlocked (for example by pushing the device against the skin) to trigger a skin sensor to place the device in into unlocked 1212 state. In some embodiments, an adhesive is connected to the skin sensor such that placing the skin sensor onto the user engages the device to an engaged state 1211 before unlocking the device. Alternatively or additionally, the device may be unlocked before attaching to the subject. For example, skin may extend out from a skin contact surface and/or the skin sensor may be triggered before engaging the device to the subject (e.g. the unlocked 1212 state may precede the engaged 1211 state). Optionally, in the unlocked 1212 state, an activation control is used to move the device into an activated 1216 state (for example, by inserting a needle into the subject). Optionally, the activated 1216 device delivers the drug in a delivering 1217 state. In some embodiments, at the end of delivery and/or when the device is removed from the subject the device stops delivering and/or enters a deactivated 1218 state. Optionally, deactivation may be irreversible and/or reversible.

In some embodiments, an injector may be supplied to a user in a locked state. For example, the user may prepare the device by opening a package, unpacking the device, priming the device, and/or activating the device. For example, preparing the device may include removing a protective cap and/or removing a protective covering. For example, an adhesive protector may be peeled from a skin contact surface on the base of the injector and/or on the housing of the injector. The presence of the adhesive and/or the act of removing the adhesive cover optionally primes and/or activates the device. Optionally, during unpacking and/or preparing the device, the device may be connected to a power source and/or a computing device (for example, a personal computing device of the user). For example, a set of live instructions may be displayed. Optionally, preparing and/or priming the device places the device into a skin detection state. For example, removing the needle cap and/or adhesive protector may extend a base and/or a skin sensor of the device. For example, allowing the base of the device and/or the skin sensor to collapse toward the housing of the device when attached to an injection site.

In some embodiments, before activation the device enters a protected 1220 state. For example in the protected 1220 state, a needle tip may be locked and/or protected. For example, a needle tip may be surrounded on three sides by a housing and/or by a needle shield. Optionally, in the skin detection state the needle is locked in the protective state until the injector interacts with and/or is connected to an injection site. For example, the needle may remain in the locked position until the base of the injector is attached to an injection site and/or the housing of the injector is brought together with the base. Optionally, after use and/or after protecting the device, the device can be discarded. For example, the device may fit legal requirements for disposal in municipal garbage (in a disposed 1222 state).

In some embodiments, the base of the injector may be attached to the skin of a subject (for example at an injection zone) while the device is in the skin detection state. Optionally, after attachment, the housing is moved towards the base and/or the skin to facilitate activation of the device. For example, facilitating activation of the device may include triggering needle insertion. Alternatively or additionally, facilitating activation of the device may include unlocking an activation switch and/or a needle insertion trigger. Alternatively and/or additionally, attaching the base and moving the housing towards the skin may be a continuous process. For example, as the user pushes the prepared device onto the skin, first the contact surface of the base of the device contacts the skin and/or then the housing is moved toward the base and/or the skin.

In some embodiments, in the skin detection state, prior to activation, the skin contact surface of the injector may be biased away (for example outward) from the housing of the injector.

In some embodiments, an attachment mechanism of a drug delivery device may be interlocked to a needle driver and/or a needle extension mechanism. For example, pushing the device onto a delivery site moves a needle with respect to the skin contact surface and/or causes a needle to move longitudinally (for example in an arc trajectory) from a protected position (for example inside the housing) to an extended position (for example with a point projecting outward from a skin attachment surface from the housing and/or from a delivery interface). Optionally, when the device is removed from the delivery site, the delivery interface may be extended away from the housing. This optionally moves and/or locks a needle point into a protected position.

In some embodiments, in the skin detection condition, a needle of an injector is substantially perpendicular to a skin contact surface (for example, needle may range between 0 to 2 degrees and/or 2 to 5 degrees and/or 5 to 10 degrees and/or 10 to 20 degrees and/or 20 to 45 degrees from normal to the skin contact surface). For example, the orientation of the needle to the surface may facilitate preparation of the device for example including removal of a needle cap and/or adhesive protector.

In the active state, a sharp needle tip optionally extends out from the housing and/or through a skin contact surface of the injector. For example, the needle tip may project past the skin contact surface into the skin of a subject. A medicinal substance, for example a drug, may be injected through a needle into the subject. Drug delivery is optional through a hypodermic needle into the subject.

Optionally, pulling a delivery device away from an injection zone of a subject may extend the delivery interface and/or base on a device away from a housing of the device. Optionally, when the housing of the device is distanced away from a skin contact surface, a needle driver may be triggered to retract the needle into a protected location. Optionally, triggering retraction may include unlocking a needle release mechanism of the needle driver and/or initiating a needle release mechanism of the needle driver. For example, the needle may be retracted into the housing of the device.

Optionally, a delivery interface is biased away from the housing. Biasing may extend the interface away from the housing and/or trigger whenever there is no force preventing extension. For example, the interface may extend away from the housing when the device is separated from the skin regardless of whether the housing is pulled away or the separation is due to other factors (for example pealing the adhesive from the skin). Alternatively or additionally, the interface may be biased toward the housing. For example, extension of the interface away from the housing may be due to adhesive forces pulling the contact surface towards the skin as the housing is pulled away from the skin.

In some embodiments, the handle is included for intuitive preparation of the injector. For example, a pull ring handle is connected to a needle cover and/or adhesive cover. The handle optionally supplies an intuitive clue to a user that he should remove the needle cover and/or adhesive cover (for example, priming the device) before placing the contact surface against the skin. For example, a skin sensor may be covered and/or locked in a disengaged state (for example, extended away from the housing) and/or an activation switch (for example, a button) may be locked in an inactivated position until a handle is pulled away from the injector. In some embodiments, different preparation activities are connected such that a user can perform one action and prepare multiple parts of the injector. For example, the needle cover may connect to an adhesive liner that covers a skin contact surface. Optionally, peeling off the adhesive liner from the contact surface and/or removing the needle cover are achieved with one intuitive act of pulling the handle away from the skin contact surface. Alternatively or additionally, a separate contact surfaces may share an adhesive liner and/or one adhesive liner may be supplied for multiple contact surfaces.

In some embodiments, features on the housing facilitate intuitive placement of the injector. For example, a skin contact surface that is placed on the skin may be the largest flat surface of the delivery device. Optionally, the top of the injector (opposite the skin contact surface may include a user interface, for example, a switch for example a button and/or a display for example a window). A user may intuitively understand that a display and/or button will not be attached against the skin. Optionally, sides of the injector that are not placed against the skin will be generally non-flat (e.g. rounded and/or include protrusions and/or indentations).

Exemplary Dimensions of a Drug Delivery Device

In some embodiments, the payload of a reservoir (for example a syringe) may include, for example between 0.5 and 2 ml and/or between 2 and 7 ml and/or between 7 and 6 ml and/or between 7 and 10 ml of a drug and/or more. In some embodiments, the injector may discharge the entire payload as a single dose. A drug delivery device may include, for example, a patch injector, and/or an internally powered driver to drive the plunger and/or discharge the payload.

For the sake of this application, an internally powered injector driver may be defined as a drive mechanism powered by energy stored at least temporarily within the injector. Power may be stored in a power supply, for instance as chemical potential (for example a chemical that produces an expanding gas and/or a battery) and/or mechanical potential (for example stored in an elastic member and/or a spring and/or a pressurized gas). For example, the driver may be designed to discharge the payload over a time period ranging between 1 to 20 seconds and/or between 20 to 120 seconds and/or between 120 and 600 seconds and/or between 600 seconds and an hour and/or between an hour and a day and/or longer.

In some embodiments, the apparatus may be preprogrammed to wait a fixed time delay ranging between 2 to 20 minutes and/or 20 minutes to an hour and/or an hour to 6 hours and/or 6 hours to 2 days after activation before beginning delivery of the substance. Optionally, the length of the time delay may be an estimated time for a temperature sensitive component of the apparatus to reach a preferred working temperature. For example, the temperature sensitive component may include the drug and/or a battery.

In general, discharge may be driven by a driver. An internally powered driver may be powered by various mechanisms including for example a motor, including for example a DC motor, an actuator, a brushless motor, and/or a transmission including for example a telescoping assembly and/or a threaded element and/or a gear and/or a coupling and/or an elastic mechanism (for example, a spring and/or a rubber band) and/or an expanding gas and/or a hydraulic actuator).

A drug delivery device in accordance with some embodiments of the present invention may include a reservoir part as discussed. For example, a reservoir may include a medicine container and/or a syringe. Optionally a syringe may be preloaded with medicine using standard equipment and/or in an aseptic room. A preloaded syringe may optionally include a proximal opening. A plunger may optionally seal the proximal opening and/or protect the sterility of the contents of the syringe. A sterile needle, typically hollow, may optionally be connected to the syringe barrel. For example, the hollow of the needle may be in fluid communication with the interior of the barrel.

The needle may optionally be rigidly attached to the extension at the distal end of a drug cartridge. The sterility of all and/or part of the needle may, for example, be protected by a protective cap. The protective cap may remain on the needle when the cartridge is supplied and/or installed into an injector. For example, the medicine container may optionally include a cylindrical barrel rigidly attached to a needle. In some embodiments, a plunger may slide axially along the inside of the barrel to discharge a medicine payload. For example, the medicine may be discharged through the hollow needle. The protruding tip of the needle may be oriented at an angle to the axis of the barrel.

An aspect ratio of a skin contact surface may be defined as the ratio of the length of the longest axis of the skin contact surface to the shortest axis. Optionally, the axis ratio may range between 1 to 1.5 and/or 1.5 to 2 and/or between 2 to 3 and/or greater than 3. In some embodiments, the height of the injector may range between half the length of the short axis of the base to the length of the short axis of the skin contact surface and/or between the length of the short axis of the skin contact surface to twice the length of the short axis of the skin contact surface and/or greater than the twice length of the short axis of the skin contact surface. The height of the injector may supply leverage for pivoting the adhesive off the skin of a patient after use.

In some embodiments, the force to insert the needle into the skin of a patient may range, for example, between 0.02 to 0.2 N and/or between 0.2 and 0.5 N and/or between 0.5 to 5 N. Optionally, the force required to inject the drug (for example, the force on a syringe plunger) may range, for example, between 5 to 60 N. For example, the force required to inject the drug may depend on the injection rate and/or the viscosity of the drug and/or the syringe geometry and/or the needle dimensions.

In some embodiments, a needle protection mechanism may be triggered by a linear force greater than, for example, between 10 to 60 N.

For example, the drug delivery device may include an auto-injector. The auto-injector may be activated by manually pushing with enough force to insert the needle. The device may then apply an injection force to inject a drug. Once the entire drug is injected and/or when there is an obstruction and/or occlusion, the injection force may rise until it passes a threshold triggering safeguarding of the needle and/or ending injection.

For example, in the event of an occlusion and/or at the end of delivery, the linear force generated by the device may increase to the level of up to 60 N. A needle safeguarding mechanism (for example a needle retraction mechanism) may be sensitive to the force. For example, the mechanism may include a snap that gives way at 70 N returning the needle to the retracted position.

In some embodiments, the stress to inject a medicine and/or to trigger safeguarding of a needle may include a torque. For example, injection of medicine may be driven by a plunger. The plunger may optionally be driven by a threaded assembly, for example, a threaded screw and/or teeth and/or a telescoping assembly. Optionally, the pitch of the teeth and/or an associated screw may range for example between 0.5 and 2 mm. The diameter of the screw may range for example between 2.5 and 15 mm. The torque to power injection may range for example between 0.2 and 1.0 N*cm. The trigger torque (the torque at which the needle safeguarding is triggered) may range for example between to 0.5 to 2 and/or from 2 to 7 and/or from 7 to 10 N*cm.

During injection, the linear movement of a plunger may range, for example, between 10-50 mm. The length of movement of the plunger may vary for example with the volume of medicine to be injected that may range for example between 0.5 to 3 ml.

In some embodiments, a safeguarding mechanism may be sensitive to a torque. For example, the needle may be retracted when the mechanism is exposed to a twisting moment. Optionally, discharge may be driven by a torque. For example, the driver may apply torque to a threaded element pushing a plunger. When the torque on the driver reaches a threshold value, the needle may be released and/or retracted and/or a needle shield may be deployed. Alternatively or additionally, the trigger mechanism may require both a torque and a linear force. For example, requiring both a torque and a linear stress may prevent premature activation due to momentary friction.

In some embodiments, a time of discharge may range and may depend on the fill volume and/or viscosity For example, the expected injection speeds may depend on viscosity, for example for viscosity ranging from 1 cp to 15 cp the expected injection range may range between 30 to 70 sec/1 ml, for example for viscosity ranging from 15 cp to 60 cp, the expected injection rate may range between 35 to 60 sec/ml for viscosity above 60 cp, the expected injection rate may range between 53 to 67 sec/1 ml. The maximum and/or minimum expected injection time may, for example, be the maximum and/or minimum allowed fill volume divided by an injection rate.

For example, an expected time of discharge may range, for example, between 24 to 78 seconds (for example, for between 0.8 and 1.2 ml of fluid having a viscosity ranging between 1 to 15 cp) and/or between 36 to 68 seconds (for example, for between 1.2 and 1.7 ml of fluid having a viscosity ranging between 1 to 15 cp) and/or between 51 to 92 seconds (for example, for between 1.7 and 2.3 ml of fluid having a viscosity between 1 to 15 cp) and/or between 70 to 150 seconds (for example, for 2.0 to 2.5 ml of fluid having a viscosity of between 15 and 70 cp) and/or between 120 seconds and 3 minutes for larger volumes and/or viscosities. In some embodiments, injection times may be longer. The length of the injection time may be determined by considerations other than viscosity and/or volume.

In some embodiments, the reservoir may have a length ranging for example between 20 and 72 and/or 72 and 78 mm and/or 78 and 80 mm and/or 80 and 200 mm. In some embodiments, an internal cylindrical space of a reservoir may have an average width ranging, for example, between 1 and 3 mm and/or 3 and 10 and/or 10 and 15 mm and/or 15 and 25 mm and/or 25 and 50 mm. Optionally, a reservoir may have a circular cross section such that the width is the diameter of the circle. In some embodiments, an extension may have a straight end portion with a length ranging, for example, between 1 and 3 mm or 3 and 7 mm or 7 and 8 or 8 and 10 mm or 10 and 15 mm or 15 and 50 mm. In some embodiments, the exposed straight portion of a needle may have a length ranging, for example, between 1 and 5 mm or 5 and 7 mm or 7 and 10 mm or 10 and 20 mm.

In some embodiments, an extension may have a sealing ring for a needle cap. The sealing ring may have a length ranging, for example, between 0.1 and 0.6 mm or 0.6 and 1 mm or 1 and 2.5 mm or 2.5 and 3 mm or 3 and 6 mm or 6 and 15 mm. In some embodiments, a sealing ring may have an internal cavity with a length ranging, for example, between 0.5 and 1.5 mm/or 1.5 and 2.5 mm or 2.5 and 5 mm or 5 and 10 mm.

In some embodiments, the sealing ring may have an external average width which may also be an average outer diameter ranging for example between 1 and 7 mm or 7 and 5 mm or 5 and 10 mm or 10 and 20 mm. In some embodiments, the sealing ring may have an internal average width which also may be an average inner diameter ranging, for example, between 1 and 3 mm or 3 and 7 mm or 7 and 10 mm or 10 and 18 mm. In some embodiments, the extension may have a neck (not including the sealing ring) with an average width which may be an average diameter ranging, for example, between 1 and 3 mm or 3 and 7 mm or 7 and 8 mm or 8 and 16 mm. Optionally, the neck may have a non-uniform cross section (for example an I beam and/or cross shaped cross section) and/or a tapered cross section.

For a non-uniform cross section, an average outer width may be defined as the width of the smallest oval that can enclose the neck averaged over the length of the neck. In some embodiments, a fluid path between the extension and a reservoir cavity may include a 27 gauge needle or a needle ranging between 25 and 30 gauge or a needle ranging between 20 and 25 gauge or a needle ranging between 30 and 32 gauge. In some embodiments, a needle protruding from a extension may include a 27 gauge needle or a needle ranging between 25 and 30 gauge or a needle ranging between 20 and 25 gauge or a needle ranging between 30 and 32 gauge.

It is expected that during the life of a patent maturing from this application many relevant technologies and/or materials will be developed and the scope of the terms are intended to include all such new technologies and materials a priori.

As used herein the terms "about", "approximately" and "substantially" refer to ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 7, from 1 to 5, from 2 to 7, from 2 to 6, from 3 to 6 etc., as well as individual numbers within that range, for example, 1, 2, 3, 7, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents, and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

We claim:

1. A method of operating a drug delivery device initially disposed within a packaging, the drug delivery device having a gripping interface, a needle with a sterile tip, an adhesive liner, a cover protecting sterility of the tip, the cover being attached to said packaging and extending through said adhesive liner, and an adhesive skin contact surface covered by said adhesive liner, the method comprising the steps of:

grasping the gripping interface of the drug delivery device;

removing the drug delivery device from said packaging while continuing said grasping, thereby simultaneously removing said cover from said drug delivery device;

removing said adhesive liner from said adhesive skin contact surface; and adhering the drug delivery device to a skin of a subject while continuing said grasping.

2. The method of claim 1, wherein said removing the drug delivery device step includes anchoring the cover to an anchor other than a human hand and pulling said drug delivery device away from the anchor.

3. The method of claim 2, wherein said needle tip is concealed behind said adhesive skin contact surface and wherein said needle tip remains concealed after said removing steps.

4. The method of claim 1, wherein the cover includes the adhesive liner covering the adhesive skin contact surface and wherein said removing the adhesive liner step includes peeling said adhesive liner from said adhesive skin contact surface.

5. The method of claim 1, wherein the drug delivery device further includes a control interface and said grasping step is performed with one hand while maintaining at least one digit of the one hand free and positioned to manipulate the control interface.

6. The method of claim 5, wherein said control interface includes a button.

7. The method of claim 6, further comprising the step of pushing said button toward said adhesive skin contact surface.

8. The method of claim 1, wherein the removing the drug delivery device step further comprises removing a battery isolator from the drug delivery device to power the drug delivery device, the battery isolator being attached to said packaging.

9. The method of claim 1, wherein he removing the drug delivery device step further comprises removing a battery isolator from the drug delivery device to power the drug delivery device, the battery isolator being attached to said cover.

10. The method of claim 1, wherein said cover is attached to said adhesive liner such that said removing steps occur simultaneously.

11. A method of priming of a drug delivery device for a user using one hand, the drug delivery device including a gripping interface, a sterile delivery interface including an adhesive skin contact surface and a cover retaining a sterility of at least part of the delivery interface, the method comprising the steps of:

Grasping the gripping interface of the drug delivery device with the one hand while the cover protects sterility of the delivery interface and while said drug delivery device is located at least partially inside of a packaging;

anchoring the cover to an anchor other than a human hand;

removing said drug delivery device from the packaging prior to said anchoring while continuing said grasping; and pulling said drug delivery device away from the anchor with the one hand to separate the cover from the drug delivery device while continuing said grasping.

12. The method of claim 11, wherein said anchoring step includes holding the cover with a mouth.

13. The method of claim 11, wherein said at least part of the delivery interface includes a needle tip concealed behind said adhesive skin contact surface and wherein said needle tip remains concealed after said cover is separated from the drug delivery device.

14. The method of claim 11, wherein the cover includes an adhesive liner covering the adhesive skin contact surface and wherein said pulling step comprises peeling said adhesive liner from said adhesive skin contact surface.

15. The method of claim 11, further comprising the step of adhering the adhesive skin contact surface to the skin of the subject while continuing said grasping.

16. The method of claim 11, further comprising the steps of:

opening the packaging with the one hand prior to said grasping, and exposing the gripping interface of the drug delivery device as a result of said opening.

17. The method of claim 11, wherein the drug delivery device includes a control interface and said grasping step is performed while maintaining at least one digit of the one hand free and positioned to manipulate the control interface.

* * * * *